(12) United States Patent
Feuerstein et al.

(10) Patent No.: US 9,795,692 B2
(45) Date of Patent: Oct. 24, 2017

(54) OCULAR DETECTION OF AMYLOID PROTEINS

(71) Applicant: SYSTEM OF SYSTEMS ANALYTICS, INC., Fairfax, VA (US)

(72) Inventors: Giora Feuerstein, Bryn Mawr, PA (US); Richard Cliff, Vienna, VA (US)

(73) Assignee: SYSTEM OF SYSTEMS ANALYTICS, INC., Fairfax, VA (US)

(*) Notice: Subject to any disclaimer, the term of this patent is extended or adjusted under 35 U.S.C. 154(b) by 161 days.

(21) Appl. No.: 14/296,721

(22) Filed: Jun. 5, 2014

(65) Prior Publication Data
US 2015/0125396 A1 May 7, 2015

Related U.S. Application Data

(63) Continuation of application No. 14/113,056, filed as application No. PCT/US2012/035193 on Apr. 26, 2012, now abandoned.

(60) Provisional application No. 61/479,677, filed on Apr. 27, 2011.

(51) Int. Cl.
| | | |
|---|---|---|
| *A61K 51/00* | (2006.01) | |
| *A61M 36/14* | (2006.01) | |
| *A61K 49/00* | (2006.01) | |
| *G01N 33/68* | (2006.01) | |
| *A61B 5/00* | (2006.01) | |
| *A61B 3/12* | (2006.01) | |

(52) U.S. Cl.
CPC ........ *A61K 49/0056* (2013.01); *A61B 5/4088* (2013.01); *A61K 49/006* (2013.01); *A61K 49/0021* (2013.01); *G01N 33/6896* (2013.01); *A61B 3/12* (2013.01); *G01N 2800/2821* (2013.01)

(58) Field of Classification Search
CPC ............... A61K 49/00; A61K 49/0056; A61K 49/0021; A61B 5/4088; A61B 3/12; G01N 33/6896; G01N 2800/2821
USPC .......... 424/1.11, 1.65, 1.69, 1.81, 1.85, 1.89, 424/9.1, 9.2, 9.3, 9.4, 9.5, 9.6; 154/1, 154/1.1; 530/300
See application file for complete search history.

(56) References Cited

U.S. PATENT DOCUMENTS

| | | | |
|---|---|---|---|
| 7,107,092 B2 * | 9/2006 | Goldstein | A61B 5/0059 351/214 |
| 7,108,982 B1 * | 9/2006 | Hageman | G01N 33/6893 435/4 |
| 7,166,471 B2 | 1/2007 | Orser et al. | |
| 7,625,560 B2 * | 12/2009 | Basi | C07K 16/18 424/145.1 |
| 7,691,639 B2 | 4/2010 | Orser et al. | |
| 8,062,895 B2 | 11/2011 | Orser et al. | |
| 8,372,593 B2 | 2/2013 | Orser et al. | |
| 8,673,579 B2 | 3/2014 | Orser et al. | |
| 2004/0152068 A1 | 8/2004 | Goldstein et al. | |
| 2009/0238754 A1 | 9/2009 | Wegrzyn et al. | |
| 2009/0274621 A1 | 11/2009 | Wegrzyn et al. | |
| 2010/0233095 A1 | 9/2010 | Duan et al. | |
| 2012/0282169 A1 * | 11/2012 | Duan | A61K 49/0021 424/1.11 |

FOREIGN PATENT DOCUMENTS

| | | |
|---|---|---|
| DE | 10 2007 061987 A1 | 6/2009 |
| EP | 2 420 179 A2 | 2/2012 |
| WO | WO 2011/038892 A1 | 4/2011 |

OTHER PUBLICATIONS

U.S. Appl. No. 14/484,683, filed Sep. 12, 2014, Orser et al.
U.S. Appl. No. 14/299,432, filed Jun. 9, 2014, Duan et al.
International Search Report dated Nov. 6, 2012 in application No. PCT/US2012/035193.

* cited by examiner

*Primary Examiner* — D L Jones
(74) *Attorney, Agent, or Firm* — Foley & Lardner LLP

(57) ABSTRACT

Described are methods for the detection, in the eye of an individual, of protein aggregates or other misfolded proteins associated with disease using peptide or peptide mimic probes that preferentially associate with the protein aggregates or misfolded proteins, which can be accomplished non-invasively.

13 Claims, 3 Drawing Sheets

|  |  |  |  |  |  |  |  |  |  |  |  |  |  |  |  |  |  |  |  |  |  |  |  |
|---|---|---|---|---|---|---|---|---|---|---|---|---|---|---|---|---|---|---|---|---|---|---|---|
| WT (SEQ ID NO:1) |  |  |  | K | L | V | F | F | A | E | D | V | G | S | N | K | G | A | I | I | G | L | M | K |
| PEPTIDE 22 (SEQ ID NO:2) |  |  |  | K | L | V | F | F | A | E | D | V | G | S | N | K | H | A | I | I | E | L | M | K |
| PEPTIDE 38 (SEQ ID NO:3) |  |  |  | K | L | V | F | F | A | E | D | A | A | A | A | K | H | A | I | I | E | L | M | K |
| PEPTIDE 45 (SEQ ID NO:4) | A | A | A | K | L | V | F | F | A | E | D | V | G | S | N | K | H | A | I | I | E | L | M | K |
| I32S (SEQ ID NO:5) |  |  |  | K | L | V | F | F | A | E | D | V | G | S | N | K | G | A | I | S | G | L | M | K |
| M35A (SEQ ID NO:6) |  |  |  | K | L | V | F | F | A | E | D | V | G | S | N | K | G | A | I | I | G | L | A | K |
| E22P (SEQ ID NO:7) |  |  |  | K | L | V | F | F | A | P | D | V | G | S | N | K | G | A | I | I | G | L | M | K |
| GM6 (SEQ ID NO:8) |  |  |  | K | L | V | S | F | A | E | D | V | G | S | N | K | G | A | I | I | G | P | M | K |
| A21G (SEQ ID NO:9) |  |  |  | K | L | V | F | F | G | E | D | V | G | S | N | K | G | A | I | I | G | L | M | K |
| E22G (SEQ ID NO:10) |  |  |  | K | L | V | F | F | A | G | D | V | G | S | N | K | G | A | I | I | G | L | M | K |
| E22Q (SEQ ID NO:11) |  |  |  | K | L | V | F | F | A | Q | D | V | G | S | N | K | G | A | I | I | G | L | M | K |
| E22K (SEQ ID NO:12) |  |  |  | K | L | V | F | F | A | K | D | V | G | S | N | K | G | A | I | I | G | L | M | K |
| D23N (SEQ ID NO:13) |  |  |  | K | L | V | F | F | A | E | N | V | G | S | N | K | G | A | I | I | G | L | M | K |

INDICATES CHANGE TO "WILD TYPE" Aβ SEQUENCE

FIG. 1

TABLE 3: DONOR AND DATA SUMMARY

| PATIENT # | GENDER & AGE | PRE-MORTEM DIAGNOSIS | POST-MORTEM NEUROPATHOLOGY | AD DIAGNOSIS | CAUSE OF DEATH | STAINING RESULTS |
|---|---|---|---|---|---|---|
| *SOURCE 1* | | | | | | |
| #0001 | F, 85 | N/A | HIPPOCAMPAL PYRAMIDAL CELL LAYER NFT AND PLAQUES; ENTORHINAL CORTEX CONTAINS EXTRANEURONAL TANGLES AND MANY NEURONS CONTAIN NFT | AD DEFINITE | N/A | BRAIN TISSUE: STAINING OF EXTRACELLULAR AND NEURONAL STRUCTURES |
| #0002 | M, 90 | N/A | SUBCORTICAL WHITE MATTER WELL MYELINATED, NO ALZHEIMER'S TYPE II GLIA NOTED IN NEOCORTEX AND BRAIN STEM; NO ACUTE OR CHRONIC NEURON LOSS IN HIPPOCAMPI NOR HIPPOCAMPAL SCLEROSIS | NORMAL, NON-AD | N/A | BRAIN TISSUE: NO STAINING OF EXTRACELLULAR AND NEURONAL STRUCTURES |
| #0003 | M, 60 | N/A | NOT REPORTED, MULTIPLE DRUSEN IDENTIFIED AND FOCAL PERIPHERAL CYSTOIDS DEGENERATION, DRUSEN ASSOCIATED WITH AMD | NORMAL, NON-AD | N/A | EYE TISSUE: NO LABELING OF DRUSEN |
| | | | | | | |
| *SOURCE 2* | | | | | | |
| #11-1649/0 | F, 67 | SQUAMOUS CELL CARCINOMA OF THE ESOPHAGUS | N/A | NORMAL, NON-AD | CANCER | EYE TISSUE: CILIARY RETINA BACKGROUND MILD HOMOGENEOUS, OPTIC NERVE MILD |
| #11-1755/6 | M, 73 | AD, DEMENTIA | N/A | AD | NATURAL CAUSES | EYE TISSUE: CILIARY RETINA BACKGROUND MODERATE HOMOGENEOUS, OPTIC NERVE MODERATE |
| #11-1767-8 | F, 80 | AD | N/A | AD | FAILURE TO THRIVE | EYE TISSUE: CILIARY RETINA BACKGROUND MODERATE HOMOGENEOUS, OPTIC NERVE INTENSE |

*GENDER, F=FEMALE, M=MALE*
*AD-ALZHEIMER'S DISEASE*
*NFT-NEUROFIBRILLARY TANGLES*
*AMD-AGE RELATED MACULAR DEGENERATION*

FIG. 3

SEQUENCE LISTING

<160> NUMBER OF SEQ ID NOS: 64

<210> SEQ ID NO 1
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 1

Lys Leu Val Phe Phe Ala Glu Asp Val Gly Ser Asn Lys Gly Ala Ile
1               5                   10                  15

Ile Gly Leu Met Lys
            20

<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 2

Lys Leu Val Phe Phe Ala Glu Asp Val Gly Ser Asn Lys His Ala Ile
1               5                   10                  15

Ile Glu Leu Met Lys
            20

<210> SEQ ID NO 3
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 3

Lys Leu Val Phe Phe Ala Glu Asp Ala Ala Ala Ala Lys His Ala Ile
1               5                   10                  15

Ile Glu Leu Met Lys
            20

<210> SEQ ID NO 4
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 4

Lys Ala Ala Ala Lys Leu Val Phe Phe Ala Glu Asp Val Gly Ser Asn
1               5                   10                  15

Lys His Ala Ile Ile Glu Leu Met Lys
            20                  25

<210> SEQ ID NO 5
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5

Lys Leu Val Phe Phe Ala Glu Asp Val Gly Ser Asn Lys Gly Ala Ile
1               5                   10                  15

Ser Gly Leu Met Lys
            20

<210> SEQ ID NO 6
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 6

Lys Leu Val Phe Phe Ala Glu Asp Val Gly Ser Asn Lys Gly Ala Ile
1               5                   10                  15

Ile Gly Leu Ala Lys
            20

<210> SEQ ID NO 7
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 7

Lys Leu Val Phe Phe Ala Pro Asp Val Gly Ser Asn Lys Gly Ala Ile
1               5                   10                  15

Ile Gly Leu Met Lys
            20

<210> SEQ ID NO 8
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 8

Lys Leu Val Ser Phe Ala Glu Asp Val Gly Ser Asn Lys Gly Ala Ile
1               5                   10                  15

Ile Gly Pro Met Lys
            20

<210> SEQ ID NO 9
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 9

-continued

Lys Leu Val Phe Phe Gly Glu Asp Val Gly Ser Asn Lys Gly Ala Ile
1               5                   10                  15

Ile Gly Leu Met Lys
            20

<210> SEQ ID NO 10
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 10

Lys Leu Val Phe Phe Ala Gly Asp Val Gly Ser Asn Lys Gly Ala Ile
1               5                   10                  15

Ile Gly Leu Met Lys
            20

<210> SEQ ID NO 11
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11

Lys Leu Val Phe Phe Ala Gln Asp Val Gly Ser Asn Lys Gly Ala Ile
1               5                   10                  15

Ile Gly Leu Met Lys
            20

<210> SEQ ID NO 12
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 12

Lys Leu Val Phe Phe Ala Lys Asp Val Gly Ser Asn Lys Gly Ala Ile
1               5                   10                  15

Ile Gly Leu Met Lys
            20

<210> SEQ ID NO 13
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 13

Lys Leu Val Phe Phe Ala Glu Asn Val Gly Ser Asn Lys Gly Ala Ile
1               5                   10                  15

Ile Gly Leu Met Lys
            20

```
<210> SEQ ID NO 14
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 14

Lys Leu Val Phe Phe Ala Glu Asp Val Gly Ser Asn Lys Arg Ala Ile
1               5                   10                  15

Ile Glu Leu Met Lys
            20

<210> SEQ ID NO 15
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 15

Lys Leu Val Phe Phe Ala Glu Asp Val Gly Ser Asn Lys Lys Ala Ile
1               5                   10                  15

Ile Glu Leu Met Lys
            20

<210> SEQ ID NO 16
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 16

His His Gln Lys Leu Val Phe Phe Ala Glu Asp Glu Gly Ser Arg Lys
1               5                   10                  15

His Ala Ile Glu Gly Leu Met Glu Gly Lys
            20                  25

<210> SEQ ID NO 17
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 17

Glu Ala Ala Lys Leu Val Phe Phe Ala Glu Asp Glu Gly Ser Arg Lys
1               5                   10                  15

His Ala Ile Glu Gly Leu Met Glu Gly Lys
            20                  25

<210> SEQ ID NO 18
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic probe"

<400> SEQUENCE: 18

Lys Leu Val Phe Phe Ala Glu Asp Val Gly Ser Asn Lys Gly Ala Ile
1               5                   10                  15

Ser Gly Leu Met Lys
            20

<210> SEQ ID NO 19
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 19

Lys Leu Val Phe Phe Ala Lys Asp Val Gly Ser Asn Lys His Ala Ile
1               5                   10                  15

Ile Glu Leu Met Lys
            20

<210> SEQ ID NO 20
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 20

Lys Leu Val Phe Phe Ala Gln Asp Val Gly Ser Asn Lys His Ala Ile
1               5                   10                  15

Ile Glu Leu Met Lys
            20

<210> SEQ ID NO 21
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 21

Lys Leu Val Phe Phe Ala Gly Asp Val Gly Ser Asn Lys His Ala Ile
1               5                   10                  15

Ile Glu Leu Met Lys
            20

<210> SEQ ID NO 22
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (22)..(23)
<223> OTHER INFORMATION: D-Arg

<400> SEQUENCE: 22

Lys Leu Val Phe Phe Ala Glu Asp Val Gly Ser Asn Lys Gly Ala Ile
1               5                   10                  15

Ile Gly Leu Met Lys Arg Arg
            20

<210> SEQ ID NO 23
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (22)..(23)
<223> OTHER INFORMATION: D-Arg

<400> SEQUENCE: 23

Lys Leu Val Phe Phe Ala Glu Asp Val Gly Ser Asn Lys His Ala Ile
1               5                   10                  15

Ile Glu Leu Met Lys Arg Arg
            20

<210> SEQ ID NO 24
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (1)..(2)
<223> OTHER INFORMATION: D-Arg

<400> SEQUENCE: 24

Arg Arg Lys Leu Val Phe Phe Ala Glu Asp Val Gly Ser Asn Lys His
1               5                   10                  15

Ala Ile Ile Glu Leu Met Lys Glu Glu
            20                  25

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(3)
<223> OTHER INFORMATION: Any amino acid

<400> SEQUENCE: 25

Gly Xaa Xaa Glu Gly
1               5

<210> SEQ ID NO 26
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

```
<220> FEATURE:
<221> NAME/KEY: MOD_RES
<222> LOCATION: (26)..(27)
<223> OTHER INFORMATION: D-Arg

<400> SEQUENCE: 26

Lys Ala Ala Ala Lys Leu Val Phe Phe Ala Glu Asp Val Gly Ser Asn
1               5                   10                  15

Lys His Ala Ile Ile Glu Leu Met Lys Arg Arg
            20                  25

<210> SEQ ID NO 27
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (26)..(27)
<223> OTHER INFORMATION: D-Arg

<400> SEQUENCE: 27

Lys Ala Ala Ala Lys Leu Val Phe Phe Ala Glu Asp Val Gly Ser Asn
1               5                   10                  15

Lys Gly Ala Ile Ile Gly Leu Met Lys Arg Arg
            20                  25

<210> SEQ ID NO 28
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 28

Lys Leu Val Phe Phe Ala Glu Asp Val Gly Ser Asn Lys Asp Ala Asp
1               5                   10                  15

Ile Glu Leu Met Lys
            20

<210> SEQ ID NO 29
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 29

Lys Leu Val Phe Phe Ala Glu Asp Val Gly Asp Asn Lys His Ala Ile
1               5                   10                  15

Ile Glu Leu Met Lys
            20

<210> SEQ ID NO 30
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic probe"

<400> SEQUENCE: 30

Lys Leu Val Phe Phe Ala Glu Asp Val Gly Ser Asn Lys His Ala Asp
1               5                   10                  15

Ile Glu Leu Met Lys
            20

<210> SEQ ID NO 31
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 31

Lys Leu Val Phe Phe Ala Glu Asp Val Gly Ser Asn Lys His Ala Ile
1               5                   10                  15

Ile Glu Asp Met Lys
            20

<210> SEQ ID NO 32
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 32

Lys Leu Val Phe Phe Ala Glu Asp Val Gly Ser Asn Lys Asp Ala Ile
1               5                   10                  15

Ile Glu Leu Met Lys
            20

<210> SEQ ID NO 33
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 33

Lys Leu Val Phe Phe Ala Glu Asp Val Gly Asp Asn Lys His Ala Asp
1               5                   10                  15

Ile Glu Leu Met Lys
            20

<210> SEQ ID NO 34
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 34

Lys Leu Val Ser Phe Ala Glu Asp Val Gly Ser Asn Lys His Ala Ile
1               5                   10                  15

Ile Glu Pro Met Lys
            20

<210> SEQ ID NO 35
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 35

Lys Leu Val Ser Phe Ala Glu Asp Val Gly Ser Asn Lys His Ala Ile
1               5                   10                  15

Ile Glu Leu Met Lys
            20

<210> SEQ ID NO 36
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 36

Lys Leu Val Phe Phe Ala Glu Asp Val Gly Ser Asn Lys Gly Ala Ile
1               5                   10                  15

Ile Gly Leu Met Lys
            20

<210> SEQ ID NO 37
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (23)..(25)
<223> OTHER INFORMATION: D-Arg

<400> SEQUENCE: 37

Glu Lys Leu Val Phe Phe Ala Glu Asp Val Gly Ser Asn Lys Gly Ala
1               5                   10                  15

Ile Ile Gly Leu Met Lys Arg Arg Arg
            20                  25

<210> SEQ ID NO 38
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 38

Lys Leu Val Phe Phe Ala Glu Asp Val Gly Ser Asn Lys His Ala Ile
1               5                   10                  15

Ile Glu Leu Met Lys Glu Ala Ala Ala Lys
            20                  25

<210> SEQ ID NO 39
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 39

Lys Leu Val Phe Phe Ala Glu Asp Val Gly Ser Asn Lys His Ala Ile
1               5                   10                  15

Ile Glu Leu Met Lys
            20

<210> SEQ ID NO 40
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 40

Lys Leu Val Phe Phe Ala Glu Asp Val Gly Ser Asn Lys His Ala Ile
1               5                   10                  15

Ile Glu Leu Met Lys Gly Ser Ser Gly Ser Ser Lys
            20                  25

<210> SEQ ID NO 41
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 41

Lys Leu Val Phe Phe Ala Glu Asp Val Gly Ser Asn Lys His Ala Ile
1               5                   10                  15

Ile Glu Leu Met Lys Gly Leu Val Pro Arg Gly Ser Gly Lys
            20                  25                  30

<210> SEQ ID NO 42
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 42

Lys Leu Val Phe Phe Ala Glu Asp Val Gly Ser Asn Lys His Ala Ile
1               5                   10                  15

Ile Glu Leu Met Lys Pro Ser Gly Ser Pro Lys
            20                  25

<210> SEQ ID NO 43
<211> LENGTH: 21
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 43

Lys Leu Val Phe Phe Ala Glu Asp Val Gly Ser Asn Lys His Ala Ile
1               5                   10                  15

Ile Glu Leu Met Lys
            20

<210> SEQ ID NO 44
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 44

Glu Leu Val Phe Phe Ala Glu Asp Val Gly Ser Asn Lys Gly Ala Ile
1               5                   10                  15

Ile Gly Leu Met Lys
            20

<210> SEQ ID NO 45
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 45

Glu Arg His Asp Ser Gly Tyr Glu Val His His Gln Lys Leu Val Phe
1               5                   10                  15

Phe Ala Glu Asp Val Gly Ser Asn Lys Gly Ala Ile Ile Gly Leu Met
                20                  25                  30

Val Gly Gly Val Val Ile Ala Lys
        35                  40

<210> SEQ ID NO 46
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 46

Glu Glu Phe Arg His Asp Ser Gly Tyr Glu Val His His Gln Lys Leu
1               5                   10                  15

Val Phe Phe Ala Glu Asp Val Gly Ser Asn Lys Gly Ala Ile Ile Gly
                20                  25                  30

Leu Met Lys
        35

<210> SEQ ID NO 47
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic probe"

<400> SEQUENCE: 47

Glu Ala Ala Ala Lys Leu Val Phe Phe Ala Glu Asp Glu Gly Ser Arg
1               5                   10                  15

Lys His Ala Ile Glu Gly Leu Met Glu Gly Lys
            20                  25

<210> SEQ ID NO 48
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 48

Glu His His Gln Lys Leu Val Phe Phe Ala Glu Asp Glu Gly Ser Arg
1               5                   10                  15

Lys His Ala Ile Glu Gly Leu Met Glu Gly Lys
            20                  25

<210> SEQ ID NO 49
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 49

Glu Leu Val Phe Phe Ala Glu Asp Val Gly Ser Asn Lys His Ala Ile
1               5                   10                  15

Ile Glu Leu Met Lys
            20

<210> SEQ ID NO 50
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 50

Lys Leu Val Phe Phe Ala Glu Asp Val Gly Ser Asn Lys His Ala Ile
1               5                   10                  15

Ile Glu Leu Met Trp
            20

<210> SEQ ID NO 51
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 51

Lys Leu Val Phe Phe Ala Glu Asp Val Gly Ser Asn Lys Gly Ala Ile
1               5                   10                  15

Ile Gly Leu Met Glu
            20

<210> SEQ ID NO 52
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 52

Lys Leu Val Phe Phe Ala Glu Asp Val Gly Ser Asn Lys His Ala Ile
1               5                   10                  15

Ile Glu Leu Met Glu
            20

<210> SEQ ID NO 53
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 53

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Glu

<210> SEQ ID NO 54
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 54

His His Gln Lys Leu Val Phe Phe Ala Glu Asp Glu Gly Ser Arg Lys
1               5                   10                  15

His Ala Ile Glu Gly Leu Met Glu Gly Glu
            20                  25

<210> SEQ ID NO 55
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 55

Glu Ala Ala Lys Leu Val Phe Phe Ala Glu Asp Glu Gly Ser Arg Lys
1               5                   10                  15

His Ala Ile Glu Gly Leu Met Glu Gly Glu
            20                  25

<210> SEQ ID NO 56

```
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 56

Cys Leu Val Phe Phe Ala Glu Asp Val Gly Ser Asn Lys Gly Ala Ile
1               5                   10                  15

Ile Gly Leu Met Cys
            20

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Glu Ala Ala Ala Lys
1               5

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Ser Ser Gly Ser Ser Lys
1               5

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Leu Val Pro Arg Gly Ser
1               5

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Leu Val Pro Arg Gly Ser Gly Lys
1               5

<210> SEQ ID NO 61
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Pro Ser Gly Ser Pro Lys
1               5

<210> SEQ ID NO 62
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (22)..(23)
<223> OTHER INFORMATION: D-Arg

<400> SEQUENCE: 62

Cys Leu Val Phe Phe Ala Glu Asp Val Gly Ser Asn Lys His Ala Ile
1               5                   10                  15

Ile Glu Leu Met Cys Arg Arg
            20

<210> SEQ ID NO 63
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: MOD_RES
<222> LOCATION: (22)..(23)
<223> OTHER INFORMATION: D-Arg

<400> SEQUENCE: 63

Cys Leu Val Phe Phe Ala Glu Asp Val Gly Ser Asn Lys Gly Ala Ile
1               5                   10                  15

Ile Gly Leu Met Cys Arg Arg
            20

<210> SEQ ID NO 64
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 64

Lys Leu Val Phe Phe Ala Lys Asp Val Gly Ser Asn Lys Gly Ala Ile
1               5                   10                  15

Ile Gly Leu Met Lys
            20
```

OCULAR DETECTION OF AMYLOID PROTEINS

This application claims priority to U.S. Provisional Application 61/479,677, filed on Apr. 27, 2011, the entire contents of which are incorporated herein by reference in their entirety.

BACKGROUND

The pathogenesis of misfolded protein disorders is characterized by the conversion of normal proteins into aggregation-prone β-sheet rich conformations. These conformations are implicated in amyloidogenic disease. In the case of Alzheimer's Disease (AD), self-assembly of amyloid beta (Aβ) protein into neurotoxic oligomers and fibrils is a leading postulation in regard to a major mechanism that causes AD. Other misfolded proteins associated with disease include prions in transmissible spongiform encephalopathy (TSE), cerebral amyloid angiopathy (CAA), and cerebral vascular disease (CVD); -synuclein deposits in Lewy bodies of Parkinson's disease, tau in neurofibrillary tangles in frontal temporal dementia and Pick's disease; superoxide dismutase in amylotrophic lateral sclerosis; Huntingtin in Huntington's disease; and drusen in adult macular degeneration (AMD). See, e.g., Glenner et al., *J. Neurol. Sci.* 94:1-28, 1989; Haan et al., *Clin. Neurol. Neurosurg.* 92(4): 305-310, 1990.

U.S. Pat. No. 7,166,471, US 2006/0286672, US 2005/0026165, US 2008/0171341, US 2006/0057671 and US 2008/0095706 describe peptides useful for the detection of, for example, misfolded proteins, target protein having a predominantly β-sheet secondary structure, and target protein in a specific state of self-aggregation. The peptides described herein can be used in the methods described in any of these patent documents, the contents of each of which are incorporated herein by reference in their entirety.

SUMMARY OF THE INVENTION

The present invention provides in vivo methods for detecting, in the eye of an individual, protein aggregates associated with amyloidogenic disease or other misfolded protein. In some embodiments, the methods comprise (A) administering to the individual a peptide, peptoid or peptide mimic probe, wherein the probe preferentially associates with the Aβ protein aggregates or non-Aβ misfolded protein aggregates and (B) detecting any probe associated with any protein aggregates present in the eye. In other embodiments, the methods comprise (A) administering to the individual a peptide, peptoid or peptide mimic probe, wherein the probe (i) preferentially associates with the protein aggregates and (ii) generates a detectable signal when the probe associates with the protein aggregates; and (B) detecting any detectable signal resulting from the probe associating with any protein aggregates present in the eye. In accordance with any of these embodiments, Aβ protein aggregates are detected in the optic nerve, retina, lens, ciliary body, vitreous body and/or ocular blood vessels.

In some embodiments, the probe is labeled with a detectable label. In some embodiments, the probe is labeled at separate sites with a first label and a second label, generating a signal when the probe associates with Aβ protein aggregates. In further embodiments, the sites of the first and second label are selected from (i) the N-terminus and the C-terminus; (ii) the N-terminus and a separate position other than the C-terminus; (iii) the C-terminus and a separate position other than the N-terminus; and (iv) two positions other than the N-terminus and the C-terminus.

In some embodiments, the first and second labels are excimer-forming labels. In further embodiments, the first and second labels comprise pyrene or a fluorophore/quencher pair. In alternative embodiments, the first label comprises one member of a fluorescent resonance energy transfer (FRET) pair and the second label comprises the other member of the FRET pair.

In some embodiments, the probe undergoes a conformation change upon association with the protein aggregates. In more specific embodiments, the conformation shift may be selected from the group consisting of (a) adopting a conformation upon association with the Aβ protein aggregate that increases the physical proximity of the first and second labels; (b) adopting a conformation upon association with the Aβ protein aggregate that decreases the physical proximity of the first and second labels; and (c) adopting a conformation that alters the relationship between the first and second labels.

In some embodiments, the probe is a peptide (or peptidomimetic or peptoid) probe. In further embodiments, the peptide probe consists of from 10 to 50 amino acid residues. In further embodiments, the peptide probe comprises an amino acid sequence that is at least 60%, at least 75%, at least 80%, at least 85%, at least 90%, at least 95%, or 100% identical to a β-sheet forming region of Aβ protein. In further embodiments, the peptide probe consists of from 10 to 50 amino acid residues corresponding to a β-sheet forming region of Aβ protein, wherein the amino acid sequence of the probe is at least 60%, at least 75%, at least 80%, at least 85%, at least 90%, at least 95%, or 100% identical to the corresponding region of Aβ protein. In alternative embodiments, the probe is a peptide, peptidomimetic or peptoid mimic.

In some embodiments, the probe is injected into the individual. In further embodiments, the probe is injected systemically. In alternative embodiments, the probe is injected directly into the vitreous compartment of the eye. In alternative embodiments, the probe is contacted with the conjunctiva or cornea of the eye, such as via eye drops. In alternative embodiments, the probe is administered intranasally or into the respiratory system via inhalation administration.

In some embodiments, the detecting comprises using a retinal imaging device. In further embodiments, the retinal imaging device is a slit-lamp. In further embodiments, the slit-lamp is operated with a fluoroscopic device. In some embodiments, a fundus camera is used. In alternative embodiments, the detecting comprises direct inspection using regular or laser light.

In some embodiments, the amyloidogenic disease is Alzheimer's Disease. In other embodiments, the amyloidogenic disease is age related macular degeneration of various forms (e.g., "wet" or "dry" variants), diabetes, scrapie, BSE, CJD, chronic wasting disease (CWD) and transmissible spongiform encephalopathies (TSEs).

In some embodiments, the methods comprise detecting in the eye of an individual, drusen associated with age related macular degeneration comprising: (A) administering to the individual a peptide, peptoid or peptide mimic probe, wherein said probe preferentially associates with said drusen and (B) detecting any probe associated with any drusen present in the eye.

BRIEF DESCRIPTION OF THE DRAWINGS

FIG. 1 sets forth the amino acid sequences of several peptide probes useful in the methods described herein (SEQ ID NOs:1-13).

FIG. 3 is a table (Table 3) providing staining data on select patients.

DETAILED DESCRIPTION OF THE PREFERRED EMBODIMENTS

1. Overview

Figure 2:
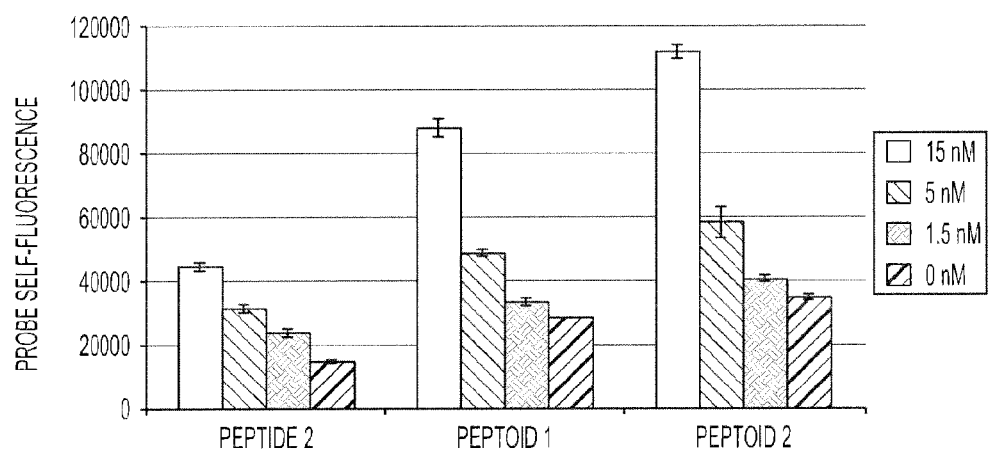
FIG. 2 illustrates the detection of synthetic Aβ oligomer in buffer by each of a peptide probe and two peptoid analogs as described herein.

We have previously described a series of conformationally dynamic peptides based on the human amyloid beta sequence that have preferential ability to detect amyloid beta aggregates or oligomers, such as in U.S. patent application Ser. No. 12/695,968, filed Jan. 28, 2010, the contents of which are incorporated herein by reference in their entirety. The amyloid beta sequence has been shown to be associated with the pathological effects associated with amyloidogenic disease, and is implicated as a marker for diseases falling under this category. The peptide probes, labeled at the N- and C-termini with, e.g., fluorescently active moieties, report the presence of amyloid beta aggregates by associating with the aggregates, detectable due to changes in the probe's fluorescence emission profile.

Misfolded proteins indicative of amyloidogenic disease, including disease caused by protein aggregates of Aβ, can be found in tissue and blood vessels in the brain. The retina of the eye, as a proxy of brain neural tissue, is connected to the brain and share blood flow. Misfolded proteins that localize in the brain are therefore expected to be found in the eye, including ocular blood vessels. Indeed, Aβ has been detected in the lens and cornea. See e.g., Goldstein et al., *The Lancet*, 361: 1258-1265 (2003); Isas et al., *Investigative Ophthalmology & Visual Science*, 51(3): 1304-1310 (2010); Kam et al., *PLoS*, 5(10): e13127 (2010); Kipfer-Kauer et al., *Current Eye Research*, 35(9): 828-834 (2010); Leger et al., *J Neuropathol Exp Neurol*, 70(1): 63-68 (2011); and Umeda et al., *FASEB*, 19: 1683-1685 (2005).

Described herein are in vivo methods for detecting, in the eye of an individual, protein aggregates associated with amyloidogenic disease. In some embodiments, the methods comprise (A) administering to the individual a peptide or peptide mimic probe, wherein the probe preferentially associates with the Aβ protein aggregates and (B) detecting any probe associated with any protein aggregates present in the eye. In other embodiments, the methods comprise (A) administering to a subject a peptide or peptide mimic probe that comprises a detectable label that generates a signal when the probe associates with any protein aggregates, and (B) detecting the signal. The methods can provide high throughput screening in an ambulatory setting, at low cost, and offer safe and, in some embodiments, non-invasive, diagnostic and prognostic tools. Further aspects and variations of the methods are described in more detail below. For convenience, the methods are described herein in terms of Aβ protein that is associated with many amyloidogenic diseases, but the invention is not limited to any specific amyloidogenic (misfolded) protein or any specific amyloidogenic disease.

2. Definitions

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" denotes any animal including humans and domesticated animals, such as fish, cats, dogs, swine, cattle, sheep, goats, horses, rabbits, and the like. "Subject" also includes experimental, laboratory animal models, such as transgenic animals used in biology and medical research. "Subject" also includes animals used in research settings, including fish, worms, mice and other small mammals, including vertebrates and non-vertebrates. A typical subject may be suspected of suffering from amyloidogenic disease, suspected of having been exposed to conditions creating a risk for amyloidogenic disease, have a genetic risk for amyloidogenic disease (e.g., individuals with family members suffering from amyloidogenic disease or having ApoE4 allele variants), or may be desirous of determining risk or status with respect to amyloidogenic disease.

As used herein, "conformation" refers to the secondary or tertiary structure of a protein or peptide, for example, an alpha-helix, random coil or β-sheet secondary structure. A "conformation shift" means any change in the conformation of the 'non-primary structure' of the protein, such as a change in the distance between the N- and C-termini (or between any other two points), folding more or less compactly, changing from predominantly one secondary structure to predominantly another secondary structure, such as from predominantly alpha helix/random coil to predominantly β-sheet, or any change in the relative amounts of different secondary structures, such as a change in the relative amounts of alpha helix/random coil and β-sheet secondary structures even without a change in the predominant secondary structure. A conformation shift can be detected on a peptide or aggregate level. As used herein, "conformation shift" includes those shifts that can be detected by any means, including standard methods for studying protein or peptide conformation, as well as indirect means, such as through label signaling discussed below, even if more direct measures of conformation, such as CD, do not reveal a change in conformation.

The term "Aβ protein" is used herein to refer to all forms of the Aβ proteins, including Aβ40 and Aβ42. "Aβ" protein also includes all naturally occurring mutants, including naturally occurring mutants known to exhibit increased tendency to form aggregates. Such mutants are known in the art, such as those disclosed in Murakami et al., *J. Biol. Chem.* 46:46179-46187, 2003, which is incorporated herein by reference in its entirety. Aβ is generated by cleaving the amyloid beta precursor protein (APP) at any of several sites, resulting in several forms of Aβ. Two abundant forms found in amyloid plaques are $Aβ_{1-40}$ (also referred to as Aβ40) and $Aβ_{1-42}$ (also referred to as Aβ42), which are produced by alternative carboxy-terminal truncation of APP. See, e.g., Selkoe et al., PNAS USA 85:7341-7345, 1988; Selkoe, *Trends Neurosci.* 16:403-409, 1993. Aβ40 and Aβ42 have identical amino acid sequences, with Aβ42 having two additional residues (Ile and Ala) at its C terminus. Although Aβ40 is more abundant, Aβ42 is the more fibrillogenic and without being bound by theory is believed to be prominent in amyloid deposits of both Alzheimer's Disease and cerebral amyloid angiopathy. See, e.g., Wurth et al., J. Mol. Biol. 319:1279-90 (2002). As noted above, all naturally occurring mutants of Aβ protein can be a target protein or serve as the basis of a reference sequence in the context of the present invention.

Target protein" is used herein to refer to any protein suitable for targeting, detection of identification by the present invention, such as those proteins capable of a conformational change, misfolding or aggregation. Target proteins may be associated with a disease state characterized by Aβ-sheet conformation as described herein, yet other conformational changes are embodied. Target proteins may be naturally occurring proteins.

As described herein, "amyloidogenic diseases" are diseases in which amyloid plaques or amyloid deposits in any form, such as amyloid β, amyloid P or other forms of amyloid, are formed in the body. Amyloid formation is found in a number of disorders, such as diabetes, AD, scrapie, BSE, CJD, chronic wasting disease (CWD), related transmissible spongiform encephalopathies (TSEs), adult macular degeneration (AMD) and other diseases disclosed herein. The invention is not limited to amyloidogenic diseases, however, and is useful in the diagnosis and treatment of any disease or condition associated with a specific conformation or aggregative state of a protein.

"Prion" refers to proteins associated with prion-based diseases. "PrP protein," "PrP," and the like are used interchangeably herein to mean both the infections particle form ("PRP$^{Sc}$") known to cause diseases (such as spongiform encephalopathies) in humans and animals, and the non-infectious form ("PRP$^C$") which, under appropriate conditions, is converted to the infectious PRP$^{Sc}$ form. Prion particles are comprised largely, if not exclusively, of PRP$^{Sc}$ molecules encoded by a PrP gene. As used herein, "prion" includes all forms of prions causing all or any of these diseases or others in any animals used, and in particular in humans and domesticated farm animals.

"Probe" refers to a peptide or peptide mimic that binds the target protein. In one embodiment, the probe associates with or binds to the target protein when the target protein has a particular conformation or is in a particular state of self-aggregation associated with amyloidogenic disease. In some embodiments, the probe undergoes a conformation shift upon association with the target protein. In other embodiments, the probe is a conformationally dynamic peptide based on the human amyloid sequence, as described in U.S. patent application Ser. No. 12/695,968, filed Jan. 28, 2010, the contents of which are incorporated herein by reference in their entirety. For convenience, the peptides and peptide mimics are referred to herein as "probes" without detracting from their utility in other contexts. These probes will be discussed in more detail below.

"Native" or "naturally occurring" proteins refer to proteins recovered from a source occurring in nature. A native protein may include post-translational modifications, including, but not limited to, acetylation, carboxylation, glycosylation, phosphorylation, lipidation, acylation, farnesylation and cleavage. "Protein," "peptide" and "polypeptide" are used interchangeably.

"Peptide mimic" is also referred to as a peptidomimic or peptidomimetic or peptoid and refers to any molecule that mimics the properties of a peptide, such as peptide structure and certain physiochemical properties. Peptide mimics include polymeric molecules that mimic the folding and/or secondary structure of a specific peptide, as well as those that mimic the biological or chemical properties of a peptide. Peptide mimics may have an amino acid backbone and contain non-natural chemical or amino acid substitutions. Peptoids may have side chains (R-groups) on the backbone amide nitrogen, instead of the alpha carbon as in peptides. This may serve one or more of several purposes: (1) peptoids may be resistant to proteolysis; (2) since peptoid secondary structure formation may not depend on hydrogen bonding, they may exhibit enhanced thermal stability as compared to peptides, and (3) the large number of available peptoid residues allows for the production of a large variety of three-dimensional structures that may aid in assay development. Alternatively, peptide mimics may have different chemical backbones, such as β-peptides, anthranilamide oligomers, oligo (m-phenylene ethynylene), oligourea, oligopyrrolinones, azatides and N-substituted glycine oligomers. Peptide mimics may have different chemical properties, such as resistance to proteases, while retaining peptide characteristics, such as peptide folding and peptide-peptide interactions (including, for example, interactions via hydrogen bonding, etc.). Any suitable peptide mimic can be used in the present invention, and include those designed and/or constructed as described in Chongsiriwatana, N. P, et al. *Proc Natl Acad Sci USA* 2008, 105, (8), 2794-9; Kirshenbaum, K., et al. *Current Opinion in Structural Biology* 1999, 9, (4), 530-535; Lee, B. C., et al., *Journal of the American Chemical Society* 2005, 127, (31), 10999-11009, which are each hereby incorporated by reference in their entirety.

"Similarity" between two polypeptides is determined by comparing the amino acid sequence of one polypeptide to the sequence of a second polypeptide. An amino acid of one polypeptide is similar to the corresponding amino acid of a second polypeptide if it is identical or a conservative amino acid substitution. Conservative substitutions include those described in Dayhoff, M. O., ed., *The Atlas of Protein Sequence and Structure* 5, National Biomedical Research Foundation, Washington, D.C. (1978), and in Argos, P. (1989) *EMBO J.* 8:779-785. For example, amino acids belonging to one of the following groups represent conservative changes or substitutions:

Ala, Pro, Gly, Gln, Asn, Ser, Thr:

Cys, Ser, Tyr, Thr;

Val, Ile, Leu, Met, Ala, Phe;

Lys, Arg, His;

Phe, Tyr, Trp, His; and

Asp, Glu.

"Homology," "homologs of," "homologous," "identity," or "similarity" refers to sequence similarity between two polypeptides, with identity being a more strict comparison. Homology and identity may each be determined by comparing a position in each sequence that may be aligned for purposes of comparison. When a position in the compared sequence is occupied by the same amino acid, then the molecules are identical at that position. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares 10% or less identity, with one of the sequences described herein. Related sequences share more than 10% sequence identity, such as at least about 15% sequence identity, at least about 20% sequence identity, at least about 30% sequence identity, at least about 40% sequence identity, at least about 50% sequence identity, at least about 60% sequence identity, at least about 70% sequence identity, at least about 80% sequence identity, at least about 90% sequence identity, at least about 95% sequence identity, or at least about 99% sequence identity.

The term "percent identity" refers to amino acid sequence identity between two peptides. Identity may be determined by comparing a position in each sequence that is aligned for purposes of comparison. When an equivalent position in one compared sequences is occupied by the same amino acid in the other at the same position, then the molecules are identical at that position; when the equivalent site occupied by the same or a similar amino acid residue (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ, FASTA and BLAST are available as part of the GCG sequence analysis package (University of Wisconsin, Madison, Wis.), and may be used with, e.g., default settings. ENTREZ is available through the National Center for Biotechnology Information, National Library of Medicine, NIH, Bethesda, Md.). In one embodiment, the percent identity of two sequences may be determined by the GCG program with a gap weight of 1, e.g., each amino acid gap is weighted as if it were a single amino acid mismatch between the two sequences. Other techniques for determining sequence identity are well known and described in the art.

3. Target Diseases

Proteins that are associated with human or animal disease when they adopt a specific conformational or self-aggregated state are known in the art. Examples of such diseases include amyloidogenic diseases, including Alzheimer's Disease (AD), age-related macular degeneration, cerebral amyloid angiopathy (CAA), and cerebral vascular disease (CVD). As used herein, "amyloidogenic diseases" are diseases in which amyloid plaques or amyloid deposits are formed in the body. Amyloid formation is found in a number of disorders, such as diabetes, AD, scrapie, bovine spongiform encephalopathy (BSE), Creutzfeldt-Jakob disease (CJD), chronic wasting disease (CWD), related transmissible spongiform encephalopathies (TSEs) and adult macular degeneration (AMD).

A variety of diseases are associated with a specific structural form of a protein (e.g., a "misfolded protein" or a self-aggregated protein), while the protein in a different structural form (e.g., a "normal protein") is not harmful. Thus, for these conditions, a β-sheet conformation could be a target structural state for detection of the disease, while an alpha-helix and/or random coil conformation could be a target structural state to confirm absence of the disease, or to identify absence of an advanced state of the disease. In many cases, the normal protein is soluble, while the misfolded protein forms lesser or insoluble aggregates. The following is a non-limiting list of diseases associated with specific structural protein states, followed parenthetically by the involved protein: Alzheimer's Disease (APP, Aβ peptide, α1-antichymotrypsin, tau, non-Aβ component, presenilin 1, presenilin 2, apoE); prion diseases, CJD, scrapie, and BSE (PrPSc); ALS (SOD and neurofilament); Pick's disease (Pick body); Parkinson's disease (α-synuclein in Lewy bodies); frontotemporal dementia (tau in fibrils); diabetes type II (amylin); multiple myeloma-plasma cell dyscrasias (IgGL-chain); familial amyloidotic polyneuropathy (transthyretin); medullary carcinoma of thyroid (procalcitonin); chronic renal failure (β2-microglobulin); congestive heart failure (atrial natriuretic factor); senile cardiac and systemic amyloidosis (transthyretin); chronic inflammation (serum amyloid A); atherosclerosis (ApoA1); familial amyloidosis (gelsolin); and Huntington's disease (Huntingtin) and adult macular degeneration (drusen and amyloid P). Also, prions in transmissible spongiform encephalopathy (TSE); cerebral amyloid angiopathy (CAA), and cerebral vascular disease (CVD); and superoxide dismutase in amylotrophic lateral sclerosis. See, e.g., Glenner et al., *J. Neural. Sci.* 94:1-28, 1989; Haan et al., *Clin. Neural. Neurosurg.* 92(4):305-310, 1990.

Often, these insoluble proteins form aggregates composed of non-branching fibrils with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions. See, e.g., Mandybur, *Acta Neuropathol.* 78:329-331, 1989; Kawai et al., *Brain Res.* 623:142-146, 1993; Martin et al., *Am. J. Pathol.* 145:1348-1381, 1994; Kalaria et al., *Neuroreport* 6:477-80, 1995; Masliah et al., *J. Neurosci.* 16:5795-5811, 1996. Other studies additionally indicate that amyloid fibrils may actually initiate neurodegeneration. See, e.g., Lendon et al., *J. Am. Med. Assoc.* 277:825-831, 1997; Yankner, Nat. Med. 2:850-852, 1996; Selkoe, *J. Biol. Chem.* 271:18295-18298, 1996; Hardy, *Trends Neurosci.* 20:154-159, 1997.

While the underlying molecular mechanism that results in protein misfolding is still not completely understood, a common characteristic for all the above mentioned neurological disorders is the propensity to form aggregates and/or fibrils which come together to form a β-sheet structure or other conformations. Fibril formation and the subsequent formation of secondary β-sheet structures associated with plaque deposits, occurs via a complex mechanism involving a nucleation stage, in which monomers of the protein associate to form fibrils, followed by extension of the fibrils at each end. For example, the proteins may self-assemble from monomers into soluble oligomers (soluble aggregates), insoluble oligomers (e.g., insoluble amorphous self-aggregates), protofibrils, and fibrils before forming non-soluble, large aggregated deposits such as plaques. Thus, peptide, protein or antibody probes that are capable of disrupting fibril formation are expected to slow the rate or completely prevent disease progression and thus be of therapeutic importance. Additionally, agents capable of associating with a particular state of the diseased protein (e.g., insoluble aggregates or fibrils) are useful diagnostic tools to detect and quantify a particular form of the misfolded protein, as well as provide insights to the presence, progression, severity and prognosis of the disease or the efficacy of drugs or compounds that are aimed at disrupting the formation of the aggregates and fibrils. Thus, highly selective peptide agents capable of associating with specific proteins in a particular state of induced or self-aggregation are useful as detection agents, in drug development, in diagnostics and as prognostic tools as well as for ultimate therapeutic applications.

Described herein are in vivo methods for detecting, in an individual's eye (including the retina and/or optic nerve and/or ocular blood vessels and/or other structures), misfolded target protein associated with diseases. Such misfolded proteins may exhibit an increase in β-sheet secondary structure or conformation and may form, for example, insoluble aggregates, fibrils or deposits such as plaques that may be hallmarks of such diseases. For convenience, the discussion below refers to the detection of "protein aggregates associated with amyloidogenic disease," but is not limited thereto and includes detection of other diseases associated with protein misfolding, aggregation and conformational change.

(i) Amyloidogenic Diseases

Amyloid beta protein (Aβ) is the primary causative agent in amyloidogenic diseases such as Alzheimer's disease (AD), cerebral amyloid angiopathy (CAA), and cerebral vascular disease (CVD).

The Aβ protein is generated by cleaving the amyloid beta precursor protein (APP) at any of several sites, resulting in several forms of Aβ. Two abundant forms found in amyloid plaques are $A\beta_{1-40}$ (also referred to as Aβ40) and Aβ42 (also referred to as Aβ42), which are produced by alternative carboxy-terminal truncation of APP. See, e.g., Selkoe et al., PNAS USA 85:7341-7345, 1988; Selkoe, *Trends Neurosci.* 16:403-409, 1993. Aβ40 and Aβ42 have identical amino acid sequences, with Aβ42 having two additional residues (Ile and Ala) at its C terminus. Although Aβ40 is more abundant, Aβ42 is the more fibrillogenic and is the major component of the two in amyloid deposits of both AD and CAA. See, e.g., Wurth et al., J. Mol. Biol. 319: 1279-90 (2002). As noted above, all naturally occurring mutants of Aβ protein can be a target protein or serve as the basis of a reference sequence in the context of the present invention.

Soluble Aβ is found in the plasma and cerebrospinal fluid of healthy individuals, and disease appears to correlate with insoluble fibrils forming plaques or aggregates found in diseased individuals. Plasma levels of Aβ42 and Aβ40 can be determined using monoclonal antibodies. In addition to the amyloid deposits in AD cases described above, AD cases can be associated with amyloid deposition in the vascular walls. See, e.g., Vinters H. V., Stroke March-April; 18(2): 311-324, 1987; Itoh Y., et al., Neurosci. Lett. 155(2):144-147, Jun. 11, 1993.

It has been discovered that in Alzheimer's Disease, amyloid protein aggregates (e.g., Aβ protein aggregates), which may form as precursors to amyloid fibrils and plaques, can be found in tissues connected to the brain, such as tissues associated with the eye (including the retina, optic nerve, and optic vessels). Without being bound by theory, it is believed that Aβ protein aggregates detected in these outlying tissues are the result of amyloid transpositions from the brain (or other extra-neuronal cells/tissues), where they originate. This transposition profile may result in a decreasing gradient of Aβ protein aggregates from the brain to the outlying tissues, such as a decreasing gradient from the brain to the optic nerve to the retina of the eye. In some embodiments, Aβ protein aggregates can move from the outlying tissues to the brain. Thus, the ability to detect Aβ protein aggregates in the eye (including the retina and/or optic nerve), can permit an early diagnosis of Alzheimer's Disease, even in patients who otherwise exhibit no other symptom of the disease. Additionally or alternatively, the level of Aβ protein aggregates detected in the eye (including the optic nerve and/or retina), can be used to assess the level of Aβ protein aggregates likely to exist in the brain.

(ii) Prion Diseases and Transmissible Spongiform Encephalopathies

Prions are infections pathogens that cause central nervous system spongiform encephalopathies in humans and animals. A potential prion precursor is a protein referred to as PrP 27-30, a 28 kilodalton hydrophobic glycoprotein that polymerizes (aggregates) into rod-like filaments found as plaques in infected brains. The normal prion protein ($PrP^C$) is a cell-surface metallo-glycoprotein that has mostly an α-helix and coiled-loop structure. The abnormal form ($PrP^{Sc}$) is a conformer that is resistant to proteases and has a secondary structure that contains predominantly β-sheets. It is believed that this conformational change in secondary structure leads to aggregation and eventual neurotoxic plaque deposition in the prion disease process.

Prion-associated diseases, also known as Transmissible Spongiform Encephalopathies or "TSEs," include scrapie of sheep and goats, chronic wasting disease of deer and elk, and bovine spongiform encephalopathy (BSE) of cattle. See, e.g., Wilesmith and Wells, *Microbiol. Immunol.* 172:21-38, 1991. Four prion diseases of humans have been identified: (1) kuru, (2) Creutzfeldt-Jakob disease (CJD), (3) Gerstmann-Strassler-Scheinker Disease (GSS), and (4) fatal familial insomnia (FFI). See, e.g., Gajdusek, D. C., *Science* 197:943-969, 1977; Medori et al. *N. Engl. J. Med.* 326:444-449, 1992. TSEs are fatal neurodegenerative diseases. These diseases are characterized by the formation and accumulation in the brain of an abnormal proteinase K resistant isoform (PrP-res) of a normal protease-sensitive, host-encoded prion protein (PrP-sen). PrP-res is formed from PrP-sen by a post-translational process involving conformational changes that convert the PrP-sen into a PrP-res molecular aggregate having a higher β-sheet content. The formation of these macromolecular aggregates of PrP-res is closely associated with TSE-mediated brain pathology, in which amyloid deposits of PrP-res are formed in the brain, which eventually becomes "spongiform" (filled with holes).

The cellular protein PrP-sen is a sialoglycoprotein encoded by a gene that, in humans, is located on chromosome 20. The PrP gene is expressed in both neural and non-neural tissues, with the highest concentration of its mRNA being found in neurons. Sequences of Prp genes are disclosed in U.S. Pat. No. 5,565,186, which is incorporated herein by reference.

4. Probes

As noted above, the peptides and peptide mimics described herein are useful, for example, for detecting target protein, such as Aβ proteins and Aβ protein aggregates, having a specific conformation or state of self-aggregation, including Aβ protein aggregates associated with amyloidogenic disease, due to preferential association with such target protein. In some embodiments, the probes undergo a conformation shift upon association with target protein. In some embodiments, the probes may not undergo a conformation shift upon association with target protein. In some embodiments, the probes are conformationally dynamic peptides based on the human amyloid beta sequence, as described in U.S. patent application Ser. No. 12/695,968. The probes also may be useful in methods of screening drug candidates for treating Alzheimer's Disease, as discussed in US 2008/0095706, the contents of which are incorporated herein by reference in their entirety.

In some embodiments, the peptide probe consists of from 10 to 50 amino acid residues. In some embodiments, the probe comprises an amino acid sequence of the target protein that undergoes a conformational shift, such as a shift from an α-helix/random coil conformation to a β-sheet conformation. For example, amino acids 16-35 of the Aβ protein are known to comprise a β-sheet forming region. Thus, the probe may comprise amino acids 16-35, or 17-35, of the Aβ protein, or an amino acid sequence that is a variant thereof. In some embodiments, the probe comprises the amino acid sequence of a β-sheet forming region of a naturally occurring mutant of the target protein, such as a mutant known to exhibit an increased tendency to adopt a β-sheet conformation and/or to form aggregates. Examples of Aβ mutants, some of which are described in Murakami, supra, include the substitutions H6R, D7N, A21G, E22G, E22P, E22Q, E22K ("Italian"), and D23N. Other Aβ mutants include, for example, natural mutants outside the 1-42 amino acid sequence, such as the Swedish (K-2N M-1 L), French (V44M), German (V44A) and London (V46I or V46G) mutants. The amino acid sequence of the peptide probe may be designed, therefore, from the target protein sequence, based on existing sequence and conformation information or, alternatively, may be readily determined experimentally.

In some embodiments, the peptide probe comprises (in various extents) an amino acid sequence of the target protein that preferentially associates with Aβ protein aggregates (e.g., soluble oligomers or soluble aggregates, insoluble oligomers or insoluble amorphous self-aggregates, or protofibrils) as compared to Aβ plaques. In other embodiments, the peptide probe comprises an amino acid sequence of the target protein that preferentially associates with higher order structures of Aβ protein, such as such fibrils and/or plaques.

In some embodiments, the peptide probe (i) consists of from 10 to 50 amino acid residues comprising an amino acid sequence that is a variant of a reference sequence consisting of an amino acid sequence of a β-sheet forming region of the target protein, (ii) is capable of adopting both a random coil/alpha-helix conformation and a β-sheet conformation, and, possibly, (iii) adopts a β-sheet conformation upon binding to target protein exhibiting a β-sheet conformation or undergoes a change in conformation that generates a detectable signal upon binding to target protein. The variant sequence may comprise one or more amino acid additions, substitutions or deletions relative to the reference sequence, such that (A) the random coil/alpha-helix conformation of the variant sequence is more stable in an oxidizing environment than a probe consisting of the reference amino acid sequence and/or (B) the distance between the N-terminus and the C-terminus of the variant sequence in a random coil/alpha-helix conformation differs from the distance between the N-terminus and the C-terminus of the variant sequence in a β-sheet conformation and/or (C) the variant sequence adopts a β-sheet conformation upon binding to target protein exhibiting a β-sheet conformation more efficiently than the reference sequence and/or (D) the variant sequence adopts a less ordered conformation upon binding to target protein exhibiting a β-sheet conformation and/or (E) the β-sheet structure of the variant sequence is less thermodynamically strong than that of the reference sequence and/or (F) the variant sequence has increased stability and/or decreased reactivity than the reference sequence and/or (G) the variant sequence has an increased hydrophilicity and/or solubility in aqueous solutions than the reference sequence and/or (H) the variant sequence has an additional Aβ binding motif than the reference sequence and/or (I) the variant sequence has an enhanced ability to form aggregates. In some embodiments, the variant sequence further comprises the addition of a lysine residue at the C-terminus.

The additions, deletions and/or substitutions as compared to the amino acid sequence of the reference sequence dictate that in some embodiments, the peptide probe may have an amino acid sequence having at least 60%, at least 75%, at least 80%, at least 85%, at least 90%, at least 95%, or 100% identity to said reference sequence. In some embodiments, the peptide probe may have an amino acid sequence with one or more additional amino acids at either terminus, or at both termini, as compared to the reference sequence. Additions, substitutions, and deletions may also be made at an internal portion of the reference sequence, or both internally and terminally.

Any of the probes described herein may be end-capped at one or both of the C-terminus and the N-terminus with a small hydrophobic peptide ranging in size from about 1 to about 5 amino acids. In other embodiments, one or both of the C-terminus and N-terminus has a lysine residue, such as to facilitate labeling. Additionally or alternatively, one or both of the C-terminus and N-terminus has a cysteine residue. Additionally or alternatively, any of the probes described herein may be modified by the substitution of a methionine residue with a residue resistant to oxidation, such as an alanine residue. Additionally or alternatively, any of the probes described herein may be modified by the substitution of at least three consecutive residues of the reference sequence with alanine residues.

Any of the probes described herein may include a dipyrene butyrate (PBA) moiety at the N-terminus and/or one extending from a lysine side chain near the C-terminus, and/or at any other site suitable for labeling. Additionally or alternatively, any of the probes described herein may have been modified to include an amide group at the C-terminus, in place of the naturally occurring carboxyl group.

In specific embodiments, the probe may consist of two point mutations (e.g., SEQ ID NO:2; SEQ ID NO:62); the addition of two d-Arginine residues (r) (e.g., SEQ ID NO:22; SEQ ID NO:56; SEQ ID NO:62); combinations of mutations described herein (e.g., SEQ ID NO:23; SEQ ID NO:62); a naturally-occurring "Italian" mutant (SEQ ID NO:56); or addition of a linker and biotin (e.g., SEQ ID NO:41).

In some embodiments, the one or more amino acid additions, substitutions or deletions may introduce a salt bridge between two residues, such as between a glutamic acid residue and a histidine residue, a glutamic acid residue and an arginine residue, and/or a glutamic acid residue and a lysine residue. Further, the amino acid additions, substitutions, or deletions may introduce an Aβ binding motif into the peptide probe, such as a GXXEG motif (SEQ ID NO:25).

As disclosed above, the variant sequence optionally may adopt either a more- or less-ordered conformation upon binding to a target protein exhibiting a β-sheet conformation. In some embodiments, for example, the target protein is Aβ protein, and the variant sequence comprises one or more substitutions selected from the group consisting of G29H, G29R, G29K, and G33E. Additionally or alternatively, the β-sheet structure of the variant sequence may be less thermodynamically strong than that of the reference sequence. In specific embodiments, the variant sequence comprises one or more substitutions selected from the group consisting of I32S, F19S, S26D, H29D, I31D, L34D, and L34P.

In accordance with any of the foregoing embodiments, the peptide probe may be conjugated to a biotin moiety, such as through a peptide linker. In specific embodiments, the peptide linker is selected from the group consisting of a flexible linker, a helical linker, a thrombin site linker and a kinked linker. In other embodiments, the peptide probe is conjugated to a biotin moiety through a side chain of an internal lysine residue. Other appropriate peptide linkers are described in the art (see, e.g., U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

For example, biotinylation can be achieved through a helical linker such as EAAAK (SEQ ID NO:57) at the C-terminus, as illustrated by AD310 (SEQ ID NO:38). In general, a helical linker includes residues that form alpha helixes, such as alanine residues. Alternatively, biotinylation can be achieved through a side chain on a lysine residue, including an internal or terminal lysine residue, as illustrated by AD313 (SEQ ID NO:39). Alternatively, biotinylation can be achieved through a flexible linker (such as GSSGSSK (SEQ ID NO:58)) at the C-terminus, as illustrated by AD314 (SEQ ID NO:40). In general, a flexible linker includes one or more glycine and/or serine residues, or other residues that can freely rotate about their phi and psi angles. Alternatively, biotinylation can be achieved through a thrombin site linker (such as a linker comprising LVPRGS (SEQ ID NO:59), such as GLVPRGSGK (SEQ ID NO:60)) at the at the C-terminus, as illustrated by AD317 (SEQ ID NO:41). Alternatively, biotinylation can be achieved through a kinked linker (such as PSGSPK (SEQ ID NO:61)) at the at the C-terminus, as illustrated by AD321 (SEQ ID NO:42). In general, kinked linkers comprise one or more proline residues, or other residues that have fixed phi and psi angles that rigidly project the biotin moiety away from the peptide probe's protein-binding motif.

Additionally or alternatively, the variant sequence may have an increased hydrophilicity and/or solubility in aqueous solutions than the reference sequence. In specific embodiments, the variant sequence comprises one or more amino acid additions or substitutions that introduce a glutamic acid residue and/or a d-arginine residue. Additionally or alternatively, the variant sequence may be conjugated to a hydrophilic moiety, such as a soluble polyethylene glycol moiety.

In some embodiments, the variant sequence comprises the substitution of at least one residue with a glutamic acid residue. In some embodiments, the variant sequence comprises the substitution of at least one residue with a histidine residue. In some embodiments, the variant sequence comprises one or more substitutions selected from the group consisting of an isoleucine residue with a serine residue; glutamic acid residue with either a proline residue, a glycine residue, a glutamine residue or a lysine residue; a phenylalanine residue with a serine residue; a leucine residue with a proline residue; an alanine residue with a glycine residue; and an aspartic acid residue with an asparagine residue.

The probe may comprise a minimum number of contiguous amino acids of the target protein, such as at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 41, at least about 42, at least about 43, at least about 44, at least about 45, at least about 46, or at least about 50 contiguous amino acids of the target protein sequence, or any range between these numbers, such as about 10 to about 25 contiguous amino acids of the target protein sequence. In some embodiments, the probe does not include the naturally occurring full-length sequence of the target protein.

The probe may comprise a maximum number of contiguous amino acids of the target protein, such as up to about 5, up to about 6, up to about 7, up to about 8, up to about 9, up to about 10, up to about 11, up to about 12, up to about 13, up to about 14, up to about 15, up to about 16, up to about 17, up to about 18, up to about 19, up to about 20, up to about 21, up to about 22, up to about 23, up to about 24, up to about 25, up to about 30, or up to about 35 contiguous amino acids of the target protein sequence, or any range between these numbers, such as about 10 to about 25 contiguous amino acids of the target protein sequence.

The reference sequence may comprise a minimum number of contiguous amino acids of the target protein, such as at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 41, at least about 42, at least about 43, at least about 44, at least about 45, at least about 46, or at least about 50 contiguous amino acids of the target protein sequence, or any range between these numbers, such as about 10 to about 25 contiguous amino acids of the target protein sequence.

The reference sequence may comprise a maximum number of contiguous amino acids of the target protein, such as up to about 5, up to about 6, up to about 7, up to about 8, up to about 9, up to about 10, up to about 11, up to about 12, up to about 13, up to about 14, up to about 15, up to about 16, up to about 17, up to about 18, up to about 19, up to about 20, up to about 21, up to about 22, up to about 23, up to about 24, up to about 25, up to about 30, or up to about 35 contiguous amino acids of the target protein sequence, or any range between these numbers, such as about 10 to about 25 contiguous amino acids of the target protein sequence.

The probes themselves may comprise at least about 5 amino acids, and may include up to about 50 amino acids, or more, or any size in between, such as about 10 amino acids to about 50 amino acids in length. In some embodiments, the probes consist of about 5 to about 50, about 10 to about 50, about 10 to about 25, about 15 to about 25, or about 20 to about 25 amino acids. In further embodiments, the probes comprise from about 17 to about 34 amino acids, including about 20 amino acids, about 21 amino acids, about 22 amino acids, about 23 amino acids, about 24 amino acids, or about 25 amino acids. Probes of different lengths may exhibit different degrees of interaction and binding to the target protein, and suitable lengths can be selected by the skilled artisan guided by the teachings herein.

In some embodiments, the probes are selected from SEQ ID NOs:1-56, or from SEQ ID NOs:1-56 or 62. In some specific embodiments, the probes are selected from the group consisting of SEQ ID NOs:2, 22, 23, 41, 56 and 62. In some embodiments, the probes are PEP-10, PEP-11 and PEP-12. Probes described in US 2008/0095706 for targeting Aβ protein, and probes designed in accordance with U.S. patent application Ser. No. 12/695,968, may be used as described herein. The contents of these applications are incorporated herein by reference in their entirety.

Exemplary peptide probes designed in accordance with the principles described above are set forth in Table 1 below. As shown by underlining in the sequences, most of the peptide sequences are based on amino acids 16-35 of the Aβ peptide (WT; SEQ ID NO:1), which is a β-sheet forming region of the Aβ peptide (others are based on longer portions of the Aβ peptide), with an added C-terminal lysine residue to facilitate labeling. The category (or categories) of the sequence variants are indicated in the table (e.g., modified to improve stability, provide a salt bridge, increase solubility, facilitate alpha-helix formation, destabilize β-sheet structure, add an Aβ binding motif, etc.). Also illustrated are options for peptide probe labeling, including different label sites and label pairs. Unless indicated otherwise, all peptides were labeled with two pyrene labels, one on the N-terminal amine, and the other on a side chain of a C-terminal lysine residue. Additionally, unless indicated otherwise, all constructs contain a C-terminal amide in place of the carboxyl group.

The following abbreviations are used in the table:
"PBA"=pyrene butyric acid
"r"=d-Arginine
"Dabcyl"=4-(4-dimethylaminophenyl) diazenylbenzoic acid
"EDANS"=5-(2'-aminoethyl)aminonaphthalene-1-sulfonic acid
"FAM"=5(6)carboxyfluorescein
"Dansyl"=5-dimethylaminonaphthalene-1-sulfonyl
"FITC"=Fluorescein isothiocyanate
"Ahx"=aminohexyl

TABLE 1

PEPTIDE PROBES

| SEQ ID NO: | Category | Name | Modification | Sequence |
|---|---|---|---|---|
| 1 | Wildtype | WT | Aβ protein residues 16-35, with added C-Terminal Lys | KLVFF AEDVG SNKGA IIGLM K |
| 6 | Stability | AD250 | M35A to replace oxidizable methionine residue | KLVFF AEDVG SNKGA IIGLA K |
| 2 | Salt Bridge | P22 | Salt bridge at G29H and G33E, also induce alpha-helix, and increase solubility | KLVFF AEDVG SNKHA IIELM K |
| 14 | | P22 v.1 | Salt bridge at G29R and G33E | KLVFF AEDVG SNKRA IIELM K |
| 15 | | P22 v.2 | Salt bridge at G29K and G33E | KLVFF AEDVG SNKKA IIELM K |
| 3 | Salt Bridge + Alpha Helix | P38 | Salt bridge at G29H and G33E; Ala substitutions to increase alpha-helicity | KLVFF AEDAA AAKHA IIELM K |
| 4 | | P45 | Salt bridge at G29H and G33E; Ala additions to increase alpha-helicity | KAAA KLVFF AEDVG SNKHA IIELM K |
| 16 | Salt Bridge + Aβ Binding Motif | P77 | Salt bridge; Additional Aβ binding motif (GxxEG; SEQ ID NO: 25); extended N-terminus | HHQ KLVFF AEDEG SRKHA IEGLM EG K |

TABLE 1-continued

| SEQ ID NO: | Category | Name | Modification | Sequence |
|---|---|---|---|---|
| 17 | | P59 | Salt bridge; Additional Aβ binding motif (GxxEG; SEQ ID NO: 25) | EAA KLVFF AEDEG SRKHA IEGLM EG K |
| 19 | Based on Naturally Occurring Mutants | Italian | P22, with E22K point mutation | KLVFF AKDVG SNKHA IIELM K |
| 20 | | Dutch | P22, with E22Q point mutation | KLVFF AQDVG SNKHA IIELM K |
| 21 | | Arctic | P22, with E22G point mutation | KLVFF AGDVG SNKHA IIELM K |
| 22 | Solubility | AD272 | WT, with 2 C-terminal dArg residues, and alternate label site | (PBA)KLVFF AEDVG SNKGA IIGLM K(PBA)rr |
| 23 | | AD316 | P22, with 2 C-terminal dArg residues, and alternate label site | PBA-KLVFF AEDVG SNKHA IIELM K(PBA)rr |
| 24 | | AD305 | P22, with 2 N-terminal dArg residues, 2 C-terminal E residues and alternate label site | rrK(PBA)LVFF AEDVG SNKHA IIELM K(PBA)EE |
| 1 | | AD274 | WT, with PEG10 at C-terminus | (PBA)KLVFF AEDVG SNKGA IIGLM K(PBA)PEG10 |
| 26 | | AD271 | P45, with two dArg residues at C-terminus | (PBA)KAAA KLVFF AEDVG SNKHA IIELM K(PBA)rr |
| 27 | Induce Alpha-Helix + Solubility | AD273 | WT, with addition of Ala stretch (for alpha-helix formation) and dArg residues (for solubility) | (PBA)KAAA KLVFF AEDVG SNKGA IIGLM K(PBA)rr |

TABLE 1-continued

PEPTIDE PROBES

| SEQ ID NO: | Category | Name | Modification | Sequence |
|---|---|---|---|---|
| 28 | Reduce Stability of B-sheet | AD323 | P22, with point mutations H29D and I31D | KLVFF AEDVG SNKDA DIELM K |
| 29 | | AD325 | P22, with point mutation S26D | KLVFF AEDVG DNKHA IIELM K |
| 30 | | AD330 | P22, with point mutation I31D | KLVFF AEDVG SNKHA DIELM K |
| 31 | | AD329 | P22, with point mutation L34D | KLVFF AEDVG SNKHA IIEDM K |
| 32 | | AD328 | P22, with point mutation H29D | KLVFF AEDVG SNKDA IIELM K |
| 33 | | AD327 | P22, with point mutation S26D, I31D | KLVFF AEDVG DNKHA DIELM K |
| 34 | | GM6 | P22, with point mutations F19S, L34P | KLVSF AEDVG SNKHA IIEPM K |
| 35 | | GM6 var. 1 | P22, with point mutation F19S | KLVSF AEDVG SNKHA IIELM K |
| 5, 18 | | I32S | Wildtype, with I32S point mutation | KLVFF AEDVG SNKGA ISGLM K |
| 36 | Label (PBA) Site | AD266 | WT, with label on side chain of N-terminal Lys | K(*PBA*)LVFF AEDVG SNKGA IIGLM K(*PBA*) |
| 37 | | AD268 | WT, with label on side chain of near N-terminal Lys; addition of solubilizing dArg and E residues | EK(*PBA*)LVFF AEDVG SNKGA IIGLM K(*PBA*)rrr |
| 38 | Biotin | AD310 | P22, biotin labeled with helical linker at C-terminus | (*PBA*)KLVFF AEDVG SNKHA IIELM K(*PBA*)EAAAK(biotin) |

TABLE 1-continued

PEPTIDE PROBES

| SEQ ID NO: | Category | Name | Modification | Sequence |
|---|---|---|---|---|
| 39 | | AD313 | P22, biotin labeled at side chain of internal Lys | (PBA)KLVFF AEDVG SNK(biotin)HA IIELM K(PBA) |
| 40 | | AD314 | P22, biotin labeled with flexible linker at C-terminus | (PBA)KLVFF AEDVG SNKHA IIELM K(PBA)GSSGSSK(biotin) |
| 41 | | AD317 | P22, biotin labeled with thrombin site linker, at C-terminus | (PBA)KLVFF AEDVG SNKHA IIELM K(PBA)GLVPRGSGK(biotin) |
| 42 | | AD321 | P22, biotin labeled with "kinked" linker at C-terminus | (PBA)KLVFF AEDVG SNKHA IIELM K(PBA)PSGSPK(biotin) |
| 2, 43 | Label/Quencher Pairs | AD326 | P22, with pyrene and Dabcyl quencher | (PBA)KLVFF AEDVG SNKHA IIELM K(Dabacyl) |
| 44 | | AD309 | WT, with EDANS and Dabcyl quencher and solubilizing E residue | E(EDANS)LVFF AEDVG SNKGA IIGLM K(Dabacyl) |
| 45 | | AD306 | Wildtype Aβ residues 5-42, with EDANS and Dabcyl quencher and solubilizing E residue | E(EDANS)R HDSGY EVHHQ KLVFF AEDVG SNKGA IIGLM VGGVV IA K(Dabacyl) |
| 46 | | AD303 | Wildtype Aβ residues 3-35, with EDANS and Dabcyl quencher and solubilizing E residue | E(EDANS)EFR HDSGY EVHHQ KLVFF AEDVG SNKGA IIGLM K(Dabacyl) |
| 47 | | AD302 | P59, with EDANS and Dabcyl quencher and solubilizing E residue | E(EDANS)AAA KLVFF AEDEG SRKHA IEGLM HGK(Dabacyl) |

TABLE 1-continued

| PEPTIDE PROBES | | | | |
|---|---|---|---|---|
| SEQ ID NO: | Category | Name | Modification | Sequence |
| 48 | | AD301 | P77, with EDANS and Dabcyl quencher and solubilizing E residue | E(EDANS)HHQ KLVFF AEDEG SRKHA IEGLM EGK(Dabacyl) |
| 49 | | AD300 | P22 with EDANS and Dabcyl quencher and solubilizing E residue | E(EDANS)LVFF AEDVG SNKHA IIELM K(Dabacyl) |
| 50 | FRET Pairs | AD295 | P22, with Dansyl and Trp | (Dansyl)KLVFF AEDVG SNKHA IIELM W |
| 51 | | AD294 | WT, with FAM and EDANS and solubilizing E residue | (FAM)KLVFF AEDVG SNKGA IIGLM E(EDANS) |
| 52 | | AD293 | P22, with FAM and EDANS and solubilizing E residue | (FAM)KLVFF AEDVG SNKHA IIELM E(EDANS) |
| 53 | | AD292 | Aβ residues 3-35, with FAM and EDANS and solubilizing E residue | (FAM)EFR HDSGY EVHHQ KLVFF AEDVG SNKGA IIGLM E(EDANS) |
| 54 | | AD291 | P77, with FAM and EDANS and solubilizing E residue | (FAM)HHQ KLVFF AEDEG SRKHA IEGLM EGE(EDANS) |
| 55 | | AD290 | P59, with FAM and EDANS, additional Ala, and solubilizing E residue | (FAM)EAA KLVFF AEDEG SRKHA IEGLM EGE(EDANS) |
| 56 | | WT17-35 | Aβ protein residues 17-35, with added N- and C-Terminal Cys | CLVFF AEDVG SNKGA IIGLMC |
| 56 | | PEP-10 | WT17-35 with FITC label | FITC-Ahx-CLVFF AEDVG SNKGA IIGLMC-NH$_2$ |
| 56 | | PEP-11 | WT17-35 with FITC and d-Arginine at C-Terminal | FITC-Ahx-CLVFF AEDVG SNKGA IIGLMCrr-NH$_2$ |

TABLE 1-continued

PEPTIDE PROBES

| SEQ ID NO: | Category | Name | Modification | Sequence |
|---|---|---|---|---|
| 62 | | PEP-12 | P-22 with FITC label, d-Arginine at C-Terminal and Histidine and Glutamic Acid substitutions | FITC-Ahx-CLVFF AEDVG SNKHA IIELMCrr-NH$_2$ |

The probe may alternatively be a peptide mimic ("peptoid") of any of the peptide probes described herein. In some embodiments, the probe is a peptide mimic that has a natural peptide backbone but has non-natural amino acids or chemical moieties. In other embodiments, the probe is a peptide mimic that has a non-peptide backbone and comprises a chemical backbone, such as a polymeric backbone. In some embodiments, a peptide mimic exhibits increased stability over the corresponding peptide.

Additional probes may be designed and tested for use in the present methods. Briefly, peptides and peptide mimics may be computationally designed to closely match hydrophobic topology and intramolecular pair contacts to wild type Aβ peptide (SEQ ID NO:1) and/or a probe with the desired characteristics as described above. Algorithms for designing such peptides and peptide mimics are known in the art. See, e.g., Mobley, D. L., et al., Structure 2009, 17, (4), 489-98; Fennell, C. J., et al., J Phys Chem B 2009; Voelz, V. A., et al., PLoS Comput Biol 2009, 5, (2), e1000281; Shell, M. S., et al., Biophys J 2009, 96, (3), 917-24; Mobley, D. L., et al., J Chem Theory Comput 2007, 3, (4), 1231-1235; Wu, G. A., et al., Structure 2008, 16, (8), 1257-66; Chorny, I., et al., J Phys Chem B 2005, 109, (50), 24056-60.

The probes described herein selectively associate with target protein. In some embodiments, the probes may undergo a conformation shift upon association with target protein. For example, in some embodiments, the probes described herein bind to Aβ protein aggregates associated with amyloidogenic disease and undergo a conformation shift upon such binding. As noted above, the conformation shift may comprise a change in the distance between the N- and C-termini of the probe (or between any other two points), folding more or less compactly, changing from predominantly one secondary structure to predominantly another secondary structure, or any change in the relative amounts of different secondary structures, or any change in the relationship between any labels on the probes. As noted above, "conformation shift" includes those shifts that can be detected by any means, including standard methods for detecting protein or peptide conformation, including indirect means, such as through label signaling discussed below, even if more direct measures of conformation, such as CD, do not reveal a change in conformation.

In some embodiments, the probe undergoes a conformation change similar to that of the target protein. For example, in some embodiments, the probes are capable of adopting both a primarily random coil/alpha-helix conformation and a primarily β-sheet conformation, and adopt a primarily β-sheet conformation upon binding to target protein exhibiting a primarily β-sheet conformation. In some embodiments the probe is provided in a primarily α-helix/random coil conformation, and undergoes a conformation shift to a primarily β-sheet conformation upon contact, binding, association and/or interaction with target protein in a primarily β-sheet conformation. In other embodiments, the probe shifts conformation by becoming more condensed, more diffuse, or adopting any different configuration. In some embodiments, the probe more closely adopts the conformation of the Aβ protein aggregates. The probe may be provided in any physiologically acceptable solution. For example, the probe may be prepared as a trifluoracetic salt and resuspended in an organic solvent, such as 100% HFIP or 50% ACN.

In other embodiments, association of the probe with target protein is detected independently of any conformational shift that may or may not occur, such as by direct detection of probe associated with target protein, such as by detection of a detectable label on probe associated with target protein. In some embodiments, the associate is temporary, such as an initial association of the probe with the target protein and a later dissociation of the probe from the target protein.

5. Labels

As noted above, the probes disclosed herein may comprise one or more detectable labels. For example, the probe may be coupled or fused, either covalently or non-covalently, to a label, with or without a linker. In some embodiments, a label is selected to permit direct detection of probe associated with target protein. Thus, for example, one or more labels may be detectable by direct detection, such as fluorescent labels, radioactive labels, etc. Such association may be current probe association with target protein or past probe association with target protein. In other embodiments, the labels are selected to permit detection of a specific conformation of the probe, such as the conformation adopted when the probe associates with Aβ protein aggregates associated with a neurodegenerative disease. In this scenario, the label may emit a first signal (or no signal) when the probe is in a first, unassociated conformation (such as a primarily random coil/alpha-helix conformation or less organized or less dense form) and a second signal, or no signal (i.e., the probe is quenched) when the probe undergoes a conformational shift upon association with target protein (such as a primarily β-sheet conformation or more organized or more dense form). The first signal and second signal may differ in one or more attributes, such as intensity, wavelength, etc. In embodiments where the signal includes emission of light, the first signal and second signal may differ in excitation wavelength and/or emission wavelength. The signal generated when the probe undergoes a conformation shift may result from interactions between labels bound to the same probe and/or may result from interactions between labels bound to different probes. As noted above, in other embodiments, the label is detectable independent of the conformation of the probe and/or independent of any conformation shift or association with the target.

In some embodiments, a peptide probe may be labeled with a detectable label at the N-terminus, the C-terminus, both termini, or at one or more positions that generate a signal when the peptide associates with target protein or adopts a β-sheet conformation or undergoes a conformation change upon binding to target protein. The peptide probe may be labeled with two or more labels, wherein the distance between two or more labels on the peptide probe when the peptide probe is bound to target protein is different than the distance when the peptide probe is not bound to target protein. The peptide probe may additionally or alternatively be labeled with a detectable label pair selected from an excimer pair, a FRET pair and a fluorophore/quencher pair. When the peptide probe is labeled with an excimer pair, such as a pyrene pair, it may emit an excimer signal when the peptide probe exhibits a β-sheet conformation. When the peptide probe is labeled with a FRET pair, such as DACIA-I/NBD, Marina Blue/NBD, Dansyl/Trp, and EDANS/FAM, it may emit a fluorescence resonance transfer (FRET) signal when the peptide probe exhibits a β-sheet conformation. When the peptide probe is labeled with a fluorophore/quencher pair, such as pyrene/Dabcyl, EDANS/Dabcyl and FAM/Dabcyl, the fluorophore signal may be quenched when the peptide probe exhibits a β-sheet conformation.

In accordance with any of the foregoing, a detectable label may be conjugated to a side chain of a terminal lysine residue of the peptide probe, and/or to a side chain of an internal lysine residue of the peptide probe.

In some embodiments, the labels and label sites are selected such that the labels do or do not interact based on the conformation of the probe, for example, such that the labels do not interact when the probe is in its unassociated conformation and do interact when the probe undergoes a conformation shift upon association with target protein, to generate a detectable signal (including quenching), or vice versa. This may be accomplished by selecting label sites that are further apart or closer together depending on the associated state of the probe, e.g., depending on whether the probe has undergone a conformation shift upon association with target protein. In some embodiments, the magnitude of the signal associated with the associated probe is directly correlated to the amount of target protein detected. Thus, the methods of the present invention permit detection and quantification of target protein.

For example, excimer, FRET or fluorophore/quencher label pairs may be used to permit detection of a specific conformation of the probe, such as the conformation adopted when the probe associates with Aβ protein aggregates associated with amyloidogenic disease. In these embodiments, the probe is labeled at separate sites with a first label and a second label, each being complementary members of an excimer, FRET or fluorophore/quencher pair.

For example, excimer-forming labels may emit their monomeric signals when the probe is in its unassociated state, and may emit their excimer signal when the probe undergoes a conformation shift that brings the labels in closer physical proximity, upon association with the target protein. Similarly, FRET labels may emit their FRET signal when the probe undergoes a conformation shift that brings the labels in closer physical proximity. On the other hand, fluorophore/quencher label pairs may emit the fluorophore signal when the probe is in its unassociated state, and that signal may be quenched when the probe undergoes a conformation shift that brings the labels in closer physical proximity. As noted above, the labels may be sited such that the opposite change in signal occurs when the probe undergoes a conformation shift upon association with the target protein.

In some embodiments, the probe is endcapped (at one or both ends of the peptide) with a detectable label. In some embodiments, the probe comprises a detectable label at or near its C-terminus, N-terminus, or both. For example, the probe may comprises a detectable label at its C-terminus, N-terminus, or both, or at other sites anywhere that generate a signal when the probe undergoes a conformation shift upon association with Aβ protein aggregate associated with amyloidogenic disease. Thus, for example, the label sites may be selected from (i) the N-terminus and the C-terminus; (ii) the N-terminus and a separate site other than the C-terminus; (iii) the C-terminus and a separate site other than the N-terminus; and (iv) two sites other than the N-terminus and the C-terminus.

In other embodiments, a peptide probe may be labeled with a detectable label at the N-terminus, the C-terminus, both termini, or at one or more positions (including a side chain) that is detectable independent of the conformation or conformational transition of the probe. In accordance with any of the foregoing, a detectable label may be conjugated to a side chain of a terminal lysine residue of the peptide probe, and/or to a side chain of an internal lysine residue of the peptide probe.

In some embodiments, the detectable label is attached to the probe by a linker. In specific embodiments, the peptide linker is selected from the group consisting of a flexible linker, a helical linker, a thrombin site linker and a kinked linker. In specific embodiments, the linker is an aminohexyl linker. In other embodiments, the peptide probe is conjugated to a linking through a side chain of an internal lysine residue. Other appropriate peptide linkers are described in the art (see, e.g., U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

In one embodiment, pyrene moieties are present at or near each terminus of the probe and the ratio of the pyrene monomer signal to the pyrene excimer signal is dependent upon the conformation of the probe, because the pyrene moieties may be separated by different distances depending on the conformation of the peptide, such as the pyrenes being in close physical proximity in the β-sheet conformation and further apart in the random coil/alpha-helix conformation. For example, the peptide adopts a β-sheet conformation in water, with the pyrene moieties in relatively close proximity (about 10 Å between the centers of the N- and C-terminal pyrene rings). In contrast, the peptide adopts an alpha-helix conformation in 40% trifluoroethanol (TFE), with the pyrene moieties further apart (about 20 Å between the centers of the N- and C-terminal pyrene rings). Thus, for example, the monomer signal may predominate when the probe is in its unassociated state, and the excimer signal may predominate when the probe undergoes a conformation shift upon association with target protein (or the excimer signal may increase without necessarily becoming predominant). Thus, the ratio of the pyrene monomer signal to the pyrene excimer signal may be measured. Pyrene moieties present at other sites on the probe also may be useful in this context, as long as excimer formation is conformation dependent.

The formation of excimers may be detected by a change in optical properties. Such changes may be measured by known fluorimetric techniques, including UV, IR, CD, NMR, or fluorescence, among numerous others, depending upon the fluorophore label. The magnitude of these changes in optical properties is directly related to the amount of probe that has adopted the conformation associated with the signal, and so is directly related to the amount of target protein or structure present.

While these embodiments have been described in detail with regard to excimer pairs, those skilled in the art will understand that similar considerations apply to FRET and fluorophore/quencher pairs.

Moreover, while these embodiments have been described with reference to the use two labels per peptide probe, it should be understood that multiple labels could be used. For example, one or more labels could be present at each labeling site, or multiple labels could be present, each at different labeling sites on the probe. In these embodiments, the labels may generate independent signals, or may be related as excimer pairs, FRET pairs, signal/quencher, etc. For example, one site might comprise one, two, three, four or more pyrene moieties and another site might comprise a corresponding quencher.

Exemplary labels for use in any of these embodiments include fluorescent agents (e.g., fluorophores, fluorescent proteins, fluorescent semiconductor nanocrystals), phosphorescent agents, chemiluminescent agents, chromogenic agents, quenching agents, dyes, radionuclides, metal ions, metal sols, ligands (e.g., biotin, streptavidin haptens, and the like), enzymes (e.g., beta-galactosidase, horseradish peroxidase, glucose oxidase, alkaline phosphatase, and the like), enzyme substrates, enzyme cofactors (e.g., NADPH), enzyme inhibitors, scintillation agents, inhibitors, magnetic particles, oligonucleotides, and other moieties known in the art. Where the label is a fluorophore, one or more characteristics of the fluorophore may be used to assess the associated state of the labeled probe. For example, the excitation wavelength of the fluorophore may differ based on whether the labeled probe is in its unassociated conformation, or in the conformation adopted upon association with target protein. In some embodiments, the emission wavelength, intensity, or polarization of fluorescence may vary based on the associated state of the labeled probe.

As used herein, a "fluorophore" is a chemical group that may be excited by light to emit fluorescence or phosphorescence. A "quencher" is an agent that is capable of quenching a fluorescent signal from a fluorescent donor. A first fluorophore may emit a fluorescent signal that excites a second fluorophore. A first fluorophore may emit a signal that is quenched by a second fluorophore. The probes disclosed herein may undergo fluorescence resonance energy transfer (FRET).

Fluorophores and quenchers may include the following agents (or fluorophores and quenchers sold under the following tradenames): 1,5 IAEDANS; 1,8-ANS; umbelliferone (e.g., 4-Methylumbelliferone); acradimum esters, 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANFPPS; Di-8-ANEPPS (non-ratio); DiA (4-Di-16-ASP); Dichlorodihydro fluorescein Diacetate (DCFH); DiD—Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; EDANS; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); a fluorescent protein (e.g., GFP (S65T); GFP red shifted (rsGFP); GFP wild type, non-UV excitation (wtGFP); GFP wild type, UV excitation (wtGFP); and GFPuv); Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indocyanine Green (ICG); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; luminol, Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant lavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TETT™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

In specific embodiments, the fluorophore label is indocyanine green (ICG), Cy3, Cy5, Cy7 or FITC. These and other directly detectable labels are useful in embodiments where the peptide probe may not undergo a conformational shift or transformation when associated with target protein.

As noted above, in some embodiments, the label comprises a pyrene moiety. As used herein, a pyrene moiety includes pyrene, which comprises four fused benzene rings or a derivative of pyrene. By pyrene derivative is meant a molecule comprising the four fused benzene rings of pyrene, wherein one or more of the pyrene carbon atoms is substituted or conjugated to a further moiety. Exemplary pyrene derivatives include alkylated pyrenes, wherein one or more of the pyrene carbon atoms is substituted with a linear or branched, substituted or unsubstituted, alkyl, alkenyl, alkynyl or acyl group, such as a $C_1$-$C_{20}$, linear or branched, substituted or unsubstituted alkyl, alkenyl, alkynyl or acyl group, where the group may be substituted with, for example, a moiety including an O, N or S atom (e.g., carbonyl, amine, sulfhydryl) or with a halogen. In some embodiments the pyrene derivative includes one or more free carboxyl groups and/or one or more free amine groups, each of which may be directly attached to a pyrene carbon atom or attached to any position on a linear or branched, substituted or unsubstituted, alkyl, alkenyl, alkynyl or acyl group as described above, such as being attached at a carbon atom that is separated from a pyrene carbon by 1 or more, such as 1 to 3, 1 to 5, or more, atoms. In some embodiments, the pyrene is substituted with one or more acetic acid moieties and/or one or more ethylamine moieties. In some embodiments, the pyrene derivative is substituted with a single methyl, ethyl, propyl or butyl group. In some embodiments, the pyrene is substituted with a short chain fatty acid, such as pyrene butyrate. In another embodiment, the pyrene is conjugated to albumin, transferring or an Fc fragment of an antibody. In some embodiments, the substituent is attached to pyrene through a carbon-carbon linkage, amino group, peptide bond, ether, thioether, disulfide, or an ester linkage. In other embodiments, the pyrene derivative is PEGylated pyrene, i.e., pyrene conjugated to polyethylene glycol (PEG). Such pyrene derivatives may exhibit a longer circulating half-life in vivo. In other embodiments, the pyrene derivative is pyrene conjugated to albumin.

In some embodiments, the label comprises a fluorescent protein which is incorporated into a probe as part of a fusion protein. Fluorescent proteins may include green fluorescent proteins (e.g., GFP, eGFP, AcGFP, TurboGFP, Emerald, Azami Green, and ZsGreen), blue fluorescent proteins (e.g., EBFP, Sapphire, and T-Sapphire), cyan fluorescent proteins (e.g., ECFP, mCFP, Cerulean, CyPet, AmCyanl, and Midoriishi Cyan), yellow fluorescent proteins (e.g., EYFP, Topaz, Venus, mCitrine, YPet, PhiYFP, ZsYellowl, and mBanana), and orange and red fluorescent proteins (e.g., Kusabira Orange, mOrange, dTomato, dTomato-Tandem, DsRed, DsRed2, DsRed-Express (T1), DsREd-Monomer, mTangerine, mStrawberry, AsRed2, mRFP1, JRed, mCherry, HcRed1, mRaspberry, HcRed-Tandem, mPlum and AQ143). Other fluorescent proteins are described in the art (Tsien, R. Y., *Annual. Rev. Biochem.* 67:509-544 (1998); and Lippincott-Schwartz et al., *Science* 300:87-91 (2003)). These and other directly detectable labels are useful in embodiments where the peptide probe may not undergo a conformational shift or transformation when associated with target protein.

As noted above, the probes may be comprised in fusion proteins that also include a fluorescent protein coupled at the N-terminus or C-terminus of the probe. The fluorescent protein may be coupled via a peptide linker as described in the art (U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

In some embodiments, the label comprises an oligonucleotide. For example, the probes may be coupled to an oligonucleotide tag which may be detected by known methods in the art (e.g., amplification assays such as PCR, TMA, b-DNA, NASBA, and the like).

In some embodiments labels useful for in vivo imaging can be used. For example, labels useful for magnetic resonance imaging, such as fluorine-18 can be used, as can chemiluminescent labels. In another embodiment, the probe is labeled with a radioactive label. For example, the label may provide positron emission of a sufficient energy to be detected by machines employed for this purpose. One example of such an entity comprises oxygen-15 (an isotope of oxygen that decays by positron emission) or other radionuclide. Another example is carbon-11. These and other directly detectable labels are useful in embodiments where the peptide probe may not undergo a conformational shift or transformation when associated with target protein, or when it is desired to detect the probe independent of any such conformation shift. Probes labeled with such labels can be administered to a patient, permitted to localize at sites containing Aβ protein aggregates, and the patient can be imaged (scanned) to detect localized probe, and thus identify sites of localized target protein. The imaging techniques that may be used include, inter alia, magnetic resonance imaging (MRI), radiography, tomography, fluoroscopy, nuclear medicine, optical imaging, encephalography and ultrasonography. Suitable labels for use in such methods are known in the art, including those discussed above.

6. Methods

As discussed above, the present invention provides in vivo methods for the detection, in an individual's eye, of Aβ protein aggregates associated with amyloidogenic disease (or other misfolded proteins). In some embodiments, the methods comprise (A) administering to the individual a peptide or peptide mimic probe, wherein the probe preferentially associates with the protein aggregates and (B) detecting the probe associated with any protein aggregates present in the eye. In other embodiments, the methods comprise (A) administering to the individual a peptide or peptide mimic probe, wherein the probe (i) preferentially associates with the protein aggregates and (ii) generates a detectable signal when the probe associates with the protein aggregates; and (B) detecting any detectable signal resulting from the probe associating with any protein aggregates present in the eye. In accordance with any of these embodiments, Aβ protein aggregates may be detected in one or more discrete regions of the eye, such as the retina and/or optic nerve and/or optic vessels. In some embodiments, the peptide or peptide mimic probe localizes at sites of Aβ protein aggregates in the eye, such as in ocular blood vessels, cornea, lens, ciliary body, optic nerve, epithelial cells, erythrocytes, or neurons in the retina.

Step (A) may comprise administration by any suitable means that will permit localization at sites of target protein in the eye, such as by direct injection, including systemic injection, intraocular injection, or direct application, including onto the eye or into the nose. The peptide or peptide mimic probe may be formulated in any composition suitable for the route of administration, e.g., in a pharmaceutically acceptable carrier for systemic injection, direct injection, or application to the conjunctiva or cornea. For example, the peptide or peptide mimic probe may be formulated in a composition for parenteral, nasal, inhalation or ocular injection/administration, in ophthalmic solution (e.g., eye drops) or in nasal solution (e.g., nasal spray or drops). The peptide or peptide mimic probe may be administered in a single dose or in multiple doses, which may be administered at different time periods.

Step (B) may comprise any detection method that detects any detectable label on the probe, or that detects any probe associated with target protein, including any detectable signal resulting from the probe associating with any protein aggregates present in the eye. In some embodiments, step (B) comprises illuminating the eye with a light source correlated with a detectable label on the probe. In some embodiments, step (B) comprises using a retinal vessel imaging device. In some embodiments, the retinal imaging device is a fundus camera that can capture near-infrared fluorescence fundus images. In some embodiments, the retinal imaging device is a slit-lamp. In some embodiments, the retinal imaging device is aided by a fluoroscopic instrument, such as a laser. In some embodiments, the signal is detected through direct inspection using regular or laser light. In some embodiments, the signal is detected using an imaging technique, such as positron emission tomography (PET), single photon emission computed tomography (SPECT), magnetic resonance imaging (MRI), radiography, tomography, fluoroscopy, nuclear medicine, optical imaging, encephalography and ultrasonography. In other embodiments, an additional step or steps is taken before step (B), such as dilating the pupil of the eye.

In some embodiments, following Step (B), an additional optional step of calculating the contrast between probe localized at different sites in the eye can be performed, such as a comparison of probe detected in the optic nerve versus probe detected in the retina.

The ability of peptide probes as described herein to localize at and detect Aβ protein aggregates in vivo in the brain has been shown and is reported, for example, in Example 11 of US 2008/0095706. Further details on in vivo methodologies are provided, for example, in US 2008/0095706, the contents of which are incorporated herein by reference in their entirety.

Any of the peptide probes (or peptide mimic probes) and any of the labels described above can be used. In specific embodiments, the peptide probe may be labeled with a detectable label, such as a fluorescent or radioactive label, wherein the detection of such label(s) is not dependent on a particular conformation or conformational change of the probe. In some embodiments, the peptide probe may be labeled with a directly detectable label and step (B) may comprise detecting the label, such as by detecting a fluorescent label, radioactive label, etc. In other embodiments, the peptide probe may be labeled with an excimer pair and step (B) may comprise detecting any increased self signal or decreased excimer signal. In other embodiments, the peptide probe may be labeled with a FRET pair and step (B) may comprise detecting any increased non-FRET fluorophore signal or decreased FRET signal. In other embodiments, the peptide probe is labeled with a fluorophore/quencher pair and step (B) may comprise detecting any increased fluorophore signal.

7. Kits

Also provided are kits comprising the probes described herein. The kits may be prepared for practicing the methods described herein. Typically, the kits include at least one component or a packaged combination of components useful for practicing a method. By "packaged combination" it is meant that the kits provide a single package that contains a combination of one or more components, such as probes, buffers, instructions for use, and the like. A kit containing a single container is included within the definition of "packaged combination." The kits may include some or all of the components necessary to practice a method disclosed herein. Typically, the kits include at least one probe in at least one container. The kits may include multiple probes which may be the same or different, such as probes comprising different sequences and/or different labels, in one or more containers. Multiple probes may be present in a single container or in separate containers, each containing a single probe.

EXAMPLES

Example 1—Peptide Probes

Probes for the detection of Aβ aggregates were designed in accordance with the principles described herein. As illustrated in Table 1, these peptide sequences are based on amino acids 17-35 of the Aβ peptide, which is a β-sheet forming region of the Aβ peptide. The reference sequence (WT; SEQ ID NO:1) corresponds to the wildtype sequence, with a terminal lysine residue added to facilitate pyrene labeling. These peptides have been shown to bind preferentially to Aβ protein and may undergo a conformation shift to generate a signal, as described in U.S. patent application Ser. No. 12/695,968. Specific exemplary peptide probes are described below in Table 2. These probes include modifications that make them more soluble in aqueous solution compared to the reference Aβ peptide sequence. These probes include a dipyrene butyrate (PBA) moiety at the N-terminus and one extending from a lysine side chain near the C-terminus. Additionally, they have been modified to include an amide group at the C-terminus, in place of the naturally occurring carboxyl group.

TABLE 2

| SEQ ID | Sequence |
|---|---|
| 1 | PBA-KLVFF AEDVG SNKGA IIGLM K(PBA)-NH$_2$ |
| 2 | PBA-KLVFF AEDVG SNKHA IIELM K(PBA)-NH$_2$ |
| 22 | PBA-KLVFF AEDVG SNKGA IIGLM K(PBA)rr-NH$_2$ |
| 23 | PBA-KLVFF AEDVG SNKHA IIELM K(PBA)rr-NH$_2$ |
| 56 | PBA-KLVFF AKDVG SNKGA IIGLM K(PBA)-NH$_2$ |
| 41 | PBA-KLVFF AEDVG SNKHA IIELM K(PBA)GLVPR GSGK(biotin)-NH$_2$ |

The ability of other probes selected and/or designed in accordance with the description herein to preferentially associate with Aβ aggregates associated with amyloidogenic disease can be assessed and confirmed by methods described in US 2008/0095706 and U.S. patent application Ser. No. 12/695,968. For example, a bead-based oligomer binding assay, in which probe-oligomer complexes are immunoprecipitated with monoclonal 6E10 antibody and protein G-agarose can be used.

The 6E10 antibody is specific to the N-terminus of Aβ 42 peptide (1-10aa), which corresponds to an epitope not found in the probe. Therefore, the antibody will only bind to full length Aβ protein which may be present, not to the probe. To perform this assay, the amyloidogenic disease sample/probe reaction mixture is equilibrated to ensure binding of 6E10 monoclonal antibody to oligomers. After brief incubation, the antibody is precipitated with protein G-agarose beads, and washed to remove all unbound proteins. The bead-associated proteins are eluted and characterized with SDS PAGE and Western blot. The level of probe binding is estimated by comparison to reference standards to confirm the presence of amyloidogenic disease-associated Aβ aggregates in the sample.

Example 2—Detection of Synthetic Aβ Aggregates Using Peptoids

Two peptoid analogs of the peptide probe of SEQ ID NO:2 were prepared and tested for their ability to interact with amyloid beta aggregates. Modeling studies suggest that these structures should form a compact structure analogous to the beta sheet structure observed in the peptide probes under aqueous conditions. Additionally, the distance between the two pyrene moieties is comparable to what is observed for peptide probes (~10-15 Å).

These two peptoids are used in an assay as shown in FIG. 2. 70 nM of each of the two peptoid probes 1 or 2 is incubated with 15, 5, 1.5 or 0 nM synthetic Aβ42 oligomer (in triplicate). The reactions are performed in 10 mM Hepes (pH 7.0) at room temperature in a final volume of 200 µL in a microtiter plate. The plate is then analyzed using a Tecan safire$^2$ fluorescence plate reader. For each sample, the self-fluorescence response (fluorescence emission from 370-385 nm) of the peptoid is plotted as a function of amyloid beta aggregate concentration. The amyloid beta aggregate dose response of the three probe structures is comparable.

A variant of these peptoids in which biotin is appended can be synthesized for use in assays, such as the plate assay described above Example 3—Detection of Amyloid Protein Aggregate in Ocular Vessels A patient is administered a labeled peptide or peptide mimic probe as described herein, by systemic injection, by direct injection into the vitreous compartment of one or both eyes, by direct application to the conjunctiva (e.g., in eye drops), or by direct application through the nose (e.g., in a nasal solution, drops or spray). The peptide or peptide mimic probe is permitted to localize to the eye and/or associate with any amyloid protein aggregates present in ocular vessels. Visualization of the individual's ocular vessels is conducted by slit-lamp (or other retinal vessel imaging devices) with the aid of fluoroscopic (LASER) instrumentation, to detect and/or quantify any labeled peptide or peptide mimic probe associated with any amyloid protein aggregates present in the ocular vessels. The detection of such probe is correlated with the amyloid burden on the targeted ocular vessels, and indicative of a diagnosis or disease state associated with the amyloid protein aggregates.

Example 4—Detection of Amyloid Protein Aggregates in Murine Brain Tissue

Probes for detecting amyloid protein aggregates in brain tissue of transgenic mice with Alzheimer's Disease (Tg AD)

were prepared in accordance with the methods described herein. Specifically, PEP-11 (SEQ ID NO: 56 labeled with FITC) was prepared and applied to Tg AD brain tissue and age-matched non-TG murine brain tissue, used as a control.

The resulting staining revealed that PEP-11 minimally stained the non-Tg control tissue, either at the dentate gyrus or midbrain locations, but stained the dentate gyms and midbrain tissue of the Tg AD tissue to a significantly greater degree. These results demonstrate that PEP-11 can specifically detect amyloid protein aggregates in brain tissue.

Example 5—Detection of Amyloid Protein Aggregates in Human Brain Tissue

PEP-11 was prepared and applied to Alzheimer's Disease brain tissue and age-matched non-Alzheimer's Disease human brain tissue, used as a control.

The resulting staining revealed that PEP-11 minimally stained the non-Alzheimer's Disease control tissue, either at the neocortex or hippocampus locations, but stained the neocortex and hippocampus tissue of the Alzheimer's Disease tissue to a significantly greater degree. These results demonstrate that PEP-11 can specifically detect amyloid protein aggregate in human brain tissue.

Example 6—Staining of Non-Congophilic Amyloid Protein Aggregates

PEP-11 was used to stain human tissue from the hippocampal region and cerebral cortex of human brain tissue from patients with and without Alzheimer's Disease. The PEP-11 stain was compared with Congo Red staining of the same regions.

FIG. 3 (Table 3) presents a subset of patients studied: (1) Patient 0001: female, age 85 with Alzheimer's Disease diagnosis, confirmed by post-mortem neuropathology indicating hippocampal pyramidal cell layer neurofibrillary tangles and plaques, entorhinal cortex containing extraneuronal tangles and many neurons containing neurofibrillary tangles; and (2) Patient 0002: male, age 90 without Alzheimer's Disease, confirmed by post-mortem neuropathology indicating subcortical white matter well myelinated, no Alzheimer's type II glia in neocortex and brain stem, no acute or chronic neuron loss in hippocampi, and no hippocampal sclerosis.

In the female patient, PEP-11 staining was seen in the extracellular and neuronal structures. In contrast, in the male patient, there was no staining of extracellular and neuronal structures.

Generally, in the hippocampal region, Congo Red stained amyloid plaques at the center of the plaques. In contrast, PEP-11 stained non-Congophilic plaque-like structures in the vicinity of the plaques (which Congo Red does not bind), not to the plaque centers themselves.

Similarly, in the cerebral cortex of patients with Alzheimer's Disease, Congo Red stained congophilic neuro-fibrillary tangles, but in contrast, PEP-11 stained non-Congophilic plaque-like structures in the vicinity of tangle neurons. Neither Congo Red nor PEP-11 stained any morphological structure within the brain parenchyma.

Overall, the PEP-11 staining appears as diffuse staining surrounding amyloid plaque centers. Without being bound by theory, it is believed that PEP-11 preferentially associates with Aβ protein aggregate precursors to the amyloid plaques that are stained by Congo Red.

Example 7—Detection of Ocular Amyloid Protein

Human eyes from donors with and without Alzheimer's Disease were obtained from the Georgia Eye Bank. The eyes were sectioned and then stained with PEP-11 or BC750 (positive control), a small molecule dye used as a probe to detect Alzheimer's Disease.

FIG. 3 (Table 3), presents a subset of patients studied: (1) Patient 0003: male, age 60 without Alzheimer's Disease, with post-mortem neuropathology indicating that patient had multiple drusen, focal peripheral cystoids degeneration and drusen associated with age-related macular degeneration; (2) Patient 11-1649/0: female, age 67 without Alzheimer's Disease (no post-mortem neuropathology information available); (3) Patient 11-1755/6: male, age 73 with Alzheimer's Disease and dementia (no post-mortem neuropathology information available); and (4) Patient 11-1767-8, female, age 80 with Alzheimer's Disease (no post-mortem neuropathology information available).

Generally, PEP-11 bound to amyloid aggregates in both the optic nerve (e.g., in the optic nerve immediately posterior to lamina cribrosa) and ciliary retina.

In patient (3), the ciliary retina background staining was moderate and homogenous and the optic nerve staining was moderate. In patient (4), the ciliary retina background staining was moderate and homogenous and the optic nerve staining was intense.

Generally, in the optic nerve, although BC750 also bound to amyloid aggregates, the intensity of binding by PEP-11 in this region of the eye was significantly greater. In the retina, BC750 appeared to stain this tissue with more intensity and less homogeneity than PEP-11, which showed ubiquitous background staining of retinal tissue, although less intensely in non-Alzheimer's Disease eyes as compared to Alzheimer's Disease eyes. However, retinal staining by BC750 was less effective than PEP-11 in distinguishing between Alzheimer's Disease tissue and non-Alzheimer's Disease tissue.

It also was observed that PEP-11 appears to stain the optic nerve of Alzheimer's Disease patients in a dose gradient manner. In particular, PEP-11 staining appears to be greatest in the brain and surrounding amyloid plaques, with less staining in the posterior optic nerve and even less staining in the sensory retina. While not wanting to be bound by theory, this staining pattern suggests that there is a concentration gradient of amyloid protein aggregate that extends from the brain (highest concentration), through the optic nerve, to the sensory retina (lowest concentration).

Generally, it was observed that PEP-11 also appears to stain drusen in patient eyes, although the drusen in patient (1) was not labeled.

Example 8—Detection of Amyloid Protein Aggregate by Fundus Camera

A patient is administered a labeled peptide or peptide mimic probe as described herein, by direct injection into the vitreous compartment of one or both eyes. The peptide or peptide mimic probe is permitted to localize to the eye and/or associate with any amyloid protein aggregates present in ocular vessels. The pupil(s) of the injected eye(s) are then dilated with mydriatic eyedrops. Once the eyedrops have had a chance to distribute, a near-IR fluorescent image from a fundus camera is taken. The image is then measured for brightness between the optic nerve-head and retina, followed by a calculation of the contrast between the optic nerve-head and retina.

The presence of a contrast between optic disk brightness and retinal brightness represents a normative index of probe localized at amyloid protein aggregates that may be precursors to amyloid plaques (i.e. fibrils). The presence of such a contrast can indicate the level of amyloid protein aggregates present in the brain.

What is claimed is:

1. A method for detecting Aβ protein aggregates in the eye of an individual, comprising:
   (A) administering to the individual a peptide probe that consists of from 10 to 50 amino acid residues and comprises an amino acid sequence that is at least 60% identical to SEQ ID NO:1, wherein said probe binds to Aβ protein aggregates and
   (B) detecting probe associated with any Aβ protein aggregates present in the eye.

2. The method of claim 1, wherein said probe is labeled with a detectable label.

3. The method of claim 2, wherein said probe is labeled at separate sites with a first detectable label and a second detectable label, and wherein said labels generate a signal when said probe binds to said Aβ protein aggregates.

4. The method of claim 3, wherein said first and second labels comprise pyrene.

5. The method of claim 1, wherein said probe comprises an amino acid sequence that is at least 85% identical to SEQ ID NO:1.

6. The method of claim 1, wherein the probe comprises an amino acid sequence selected from the group consisting of SEQ ID NO:56 and SEQ ID NO:62.

7. The method of claim 1, wherein said administering is by systemic injection, direct injection, contacting the probe with the conjunctiva or cornea of the eye, intranasal administration or inhalation administration.

8. The method of claim 1, wherein said probe binds to Aβ protein aggregates localized in a region of the eye selected from the group consisting of the optic nerve and the retina.

9. The method of claim 1, wherein said Aβ protein aggregates are detected in a region of the eye selected from the group consisting of the optic nerve, lens, ciliary body, vitreous body, the retina and ocular blood vessels.

10. The method of claim 1, wherein said detecting is conducted using a retinal imaging device, a fundus camera, a slit-lamp operated with a fluoroscopic device, or by direct inspection using regular or laser light.

11. The method of claim 1, wherein said Aβ protein aggregates are associated with an amyloidogenic disease selected from the group consisting of Alzheimer's Disease and adult macular degeneration.

12. The method of claim 11, wherein the adult macular degeneration is a wet or dry variant.

13. A method for detecting Aβ protein aggregates in the eye of an individual, comprising:
   (A) administering to the individual a peptide probe that consists of from 10 to 50 amino acid residues and comprises an amino acid sequence that is at least 60% identical to SEQ ID NO:1, wherein said probe (i) binds to Aβ protein aggregates and (ii) generates a detectable signal when said probe binds to Aβ protein aggregates; and
   (B) detecting any detectable signal resulting from said probe binding to any protein aggregates present in the eye, wherein the presence of a detectable signal indicates the presence of a condition selected from Alzheimer's Disease, age related macular degeneration, diabetes, scrapie, BSE, CJD, chronic wasting disease (CWD) and transmissible spongiform encephalopathies (TSEs).

* * * * *